US012667321B2

(12) United States Patent
Majewski et al.

(10) Patent No.: US 12,667,321 B2
(45) Date of Patent: Jun. 30, 2026

(54) TIME-OF-FLIGHT POSITRON EMISSION TOMOGRAPHY (TOFPET) ASSEMBLY AND RELATED METHOD THEREOF

(71) Applicants: University of Virginia Patent Foundation, Charlottesville, VA (US); Charalampos Tsoumpas, Leeds (GB)

(72) Inventors: Stanislaw Majewski, Charlottesville, VA (US); Bijoy Kundu, Glen Allen, VA (US); Charalampos Tsoumpas, Leeds (GB)

(73) Assignee: University of Virginia Patent Foundation, Charlottesville, VA (US)

( * ) Notice: Subject to any disclaimer, the term of this patent is extended or adjusted under 35 U.S.C. 154(b) by 686 days.

(21) Appl. No.: 16/061,416

(22) PCT Filed: Dec. 19, 2016

(86) PCT No.: PCT/US2016/067537

§ 371 (c)(1),
(2) Date: Jun. 12, 2018

(87) PCT Pub. No.: WO2017/106838

PCT Pub. Date: Jun. 22, 2017

(65) Prior Publication Data

US 2020/0261043 A1     Aug. 20, 2020

Related U.S. Application Data

(60) Provisional application No. 62/435,645, filed on Dec. 16, 2016, provisional application No. 62/362,914, (Continued)

(51) Int. Cl.
| | |
|---|---|
| *A61B 6/50* | (2024.01) |
| *A61B 5/00* | (2006.01) |
(Continued)

(52) U.S. Cl.
CPC .............. *A61B 6/502* (2013.01); *A61B 6/037* (2013.01); *A61B 6/4216* (2013.01); *G01T 1/166* (2013.01);
(Continued)

(58) Field of Classification Search
None
See application file for complete search history.

(56) References Cited

U.S. PATENT DOCUMENTS 5,825,031 A * 10/1998 Wong ..................... A61B 6/037
                                            250/363.03
6,271,525 B1     8/2001 Majewski et al.
(Continued)

FOREIGN PATENT DOCUMENTS

WO       WO 2017/091697       6/2017

*Primary Examiner* — Michael J Carey
*Assistant Examiner* — Marjan Saboktakin
(74) *Attorney, Agent, or Firm* — Robert J. Decker

(57)     ABSTRACT

A time-of-flight positron emission tomography (TOFPET) assembly for detecting lesions of a breast of a subject, wherein the subject may anatomically be defined with a median plane and chest wall-coronal plane. The assembly may comprise: a detector array having at least two or more detector segments. The detector segments may include: a scintillator for placement toward the target, the scintillator having a top edge generally closest to the subject and a detection surface wall aligned closest to surrounding the breast, a photo multiplier opposite the scintillator, and a readout connected to the photo multiplier. The assembly may also comprise a processor that receives the acquired tracer emission signals and converts the signals into a three dimensional, tomographic image reconstruction. The detector array is defined by a ring surrounding the breast and the face of ring that may be tilted to offset the chest wall-coronal plane of the subject, and wherein one of the top edges of one
(Continued)

of the detector segments is above the chest wall-coronal plane of the subject in the posterior direction.

23 Claims, 16 Drawing Sheets

Related U.S. Application Data filed on Jul. 15, 2016, provisional application No. 62/269,628, filed on Dec. 18, 2015.

(51) Int. Cl.

| | |
|---|---|
| *A61B 6/03* | (2006.01) |
| *A61B 6/42* | (2024.01) |
| *A61B 8/00* | (2006.01) |
| *A61M 5/00* | (2006.01) |
| *G01T 1/166* | (2006.01) |
| *G01T 1/202* | (2006.01) |
| *G01T 1/29* | (2006.01) |

(52) U.S. Cl.
CPC .......... *G01T 1/2023* (2013.01); *G01T 1/2985* (2013.01); *A61B 5/0066* (2013.01); *A61B 6/032* (2013.01); *A61B 8/481* (2013.01); *A61M 5/007* (2013.01)

(56) References Cited

U.S. PATENT DOCUMENTS

| | | | | |
|---|---|---|---|---|
| 6,490,476 | B1 | 12/2002 | Townsend et al. | |
| 6,552,348 | B2 | 4/2003 | Cherry et al. | |
| 6,921,901 | B1 | 7/2005 | Chai et al. | |
| 6,946,658 | B2 | 9/2005 | Tai | |
| 7,507,968 | B2 | 3/2009 | Wollenweber et al. | |
| 7,732,774 | B2 | 6/2010 | Majewski | |
| 7,917,192 | B2 | 3/2011 | Dos Santos Varela | |
| 7,961,840 | B2 | 6/2011 | Ohi et al. | |
| 8,698,087 | B2 | 4/2014 | Surti et al. | |
| 9,513,387 | B2 | 12/2016 | Henseler et al. | |
| 2001/0040219 | A1 | 11/2001 | Cherry et al. | |
| 2003/0128801 | A1 | 7/2003 | Eisenberg et al. | |
| 2004/0004188 | A1 | 1/2004 | Tai | |
| 2004/0260176 | A1 | 12/2004 | Wollenweber et al. | |
| 2008/0077005 | A1 | 3/2008 | Piron et al. | |
| 2008/0103391 | A1 | 5/2008 | Dos Santos Varela | |
| 2010/0074399 | A1* | 3/2010 | Majewski .............. | A61B 6/037 378/37 |
| 2010/0108896 | A1* | 5/2010 | Surti ......................... | G01T 1/00 250/363.04 |
| 2010/0322379 | A1 | 12/2010 | Ohi et al. | |
| 2011/0192982 | A1 | 8/2011 | Henseler et al. | |
| 2012/0068076 | A1 | 3/2012 | Daghighian | |

* cited by examiner

FIVE-SIXTH RING SCANNER

TWO-THIRD RING SCANNER

HALF RING SCANNER

TIME-OF-FLIGHT POSITRON EMISSION TOMOGRAPHY (TOFPET) ASSEMBLY AND RELATED METHOD THEREOF

RELATED APPLICATIONS

The present application is a national stage filing of International Application No. PCT/US2016/067537, filed Dec. 19, 2016, which claims benefit of priority under 35 U.S.C § 119(e) from U.S. Provisional Application Ser. No. 62/269,628, filed Dec. 18, 2015, entitled "Dynamic TOF-PET Breast Imager with Full Breast View and Related Methods Thereof," U.S. Provisional Application Ser. No. 62/362,914, filed Jul. 15, 2016, entitled "Automatic Identification and Segmentation of Breast Tumors in PET Imaging Using Dynamic Protocol and Artificial Neural Network (ANN)," and U.S. Provisional Application Ser. No. 62/435,645, filed Dec. 16, 2016, entitled "Dynamic TOFPET Breast Imager with Full Breast View and Related Methods Thereof;" the disclosures of which are hereby incorporated by reference herein in their entirety.

FIELD OF THE INVENTION

The present invention relates generally to time-of-flight positron emission tomography (TOFPET) for detecting lesions of a breast of a subject.

INTRODUCTION

Molecular imaging in the form of enhanced nuclear medicine imaging methods have been proposed for use as an adjunct to X-ray mammography. The utilization of the radiotracers that depend on biochemical factors, such as glucose metabolism instead of tumor tissue density or vascularity, promise to enhance specificity compared to methods based on non-biochemical characteristics of breast cancers. Positron emission tomography (PET) has been applied to breast cancer imaging in women with indeterminate mammograms. The utilization of tumor-avid radiotracers, such as the glucose analogue F-18 Fluorodeoxyglucose ($^{18}$FDG), and high energy of photons produced by positron annihilation (511 keV), as well as intrinsically high resolution electronic collimation taking place in the PET case results in a potentially powerful method for identifying small suspicious breast lesions even in dense, fibroglandular breasts. However the ability of standard whole body PET scanners utilizing $^{18}$FDG to detect breast lesions in patients with abnormal mammograms is limited, at least in part, due to limited spatial resolution capabilities (~4 mm to ~7 mm) and resultant poor visibility/efficiency of small lesions. These large systems are also not convenient to provide biopsy guidance, and are expensive, and the radiation dose delivered to the patient via injected dose during standard procedure is non negligible.

Specialized PET scanners were developed to address the limited capabilities of the whole body PET scanners in imaging of the breast. These dedicated breast PET imagers offer higher efficiency in detection of small cancerous breast lesions by their intrinsic high spatial resolution (1.5-2 mm) and due to their placement close to the imaged breast, permit visualization of small lesions, as well as features (structure) of large lesions, not visible with whole body PET scanners. In addition, the high detection sensitivity also means that less radiotracer is required to produce a high quality PET image, thus reducing radiation exposure to the patient, which is especially important for younger patients, and/or in longitudinal studies such as monitoring treatment effects.

However, the dedicated systems are limited by the basic geometrical problem related to the physical process of PET coincidence imaging. PET detection efficiency drops quickly at the detector edges, because of the geometrical requirement of detection of two back-to-back 511 keV annihilation gamma rays produced in the act of positron annihilation with one of the electrons of the surrounding breast tissue. This produces a sharp drop in the detection efficiency when approaching the edge plane of the system.

Therefore, while PET is a high precision modality, practically all dedicated breast PET scanners suffer from the presence of dead regions at the base of the breast. The active region at the edges of the detector modules is stopping exactly at the edge of the active material (scintillator). Only partial remedy was to physically thrust the sensitive detector edges towards the chest wall of the patient and/or make sure that the patient is lowered into the active volume of the detector.

In summary, all of the prior designs of the dedicated PET/PEM breast imagers had such positioning of the detector modules that could not provide sufficient efficiency at the base of the breast.

In light of the above, a need arises for a PET related imager that can sufficiently taking into account the natural shape of the human body, for example. Additionally, in light of the above, a need arises for a PET related detector module that can provide sufficient efficiency at the base of the breast.

Overview

An aspect of an embodiment provides, among other things, a method and system that assures careful placing in space of the detector modules around the breast, taking into account (but not limited thereto) the natural shape of the human body, for example. An aspect of an embodiment provides, among other things, a method and system that solves the problem of missing large parts of the breast tissue in the imaging field, which heretofore had not been solved.

An aspect of an embodiment provides, among other things, a method and system imager that comprises PET related detectors being placed in the different planes.

An aspect of an embodiment provides, among other things, a method and system that comprises breast PET scanners that eliminate or reduce the presence of dead regions at the base of the breast.

An aspect of an embodiment of the present invention provides, among other things, a time-of-flight positron emission tomography (TOFPET) assembly for detecting lesions of a breast of a subject, wherein the subject may anatomically be defined with a median plane and chest wall-coronal plane. The assembly may comprise: a detector array having at least two or more detector segments. The detector segments may include: a scintillator for placement toward the target, the scintillator having a top edge generally closest to the subject and a detection surface wall aligned closest to surrounding the breast, a photo multiplier opposite the scintillator, and a readout connected to the photo multiplier. The detector segments may be configured to acquire tracer emission signals from a target of the breast with a timing resolution of less than about 600 ps. The assembly may also comprise a processor that receives the acquired tracer emission signals and converts the signals into a three dimensional, tomographic image reconstruction. The detector array may be configured having the at least two segments in a ring defining a face substantially spanning across the ring.

Further, the ring surrounding the breast and the face of ring may be tilted to offset the chest wall-coronal plane of the subject; and wherein one of the top edge of one of the detector segments is above the chest wall-coronal plane of the subject in the posterior direction.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings.

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS

Figure 14:
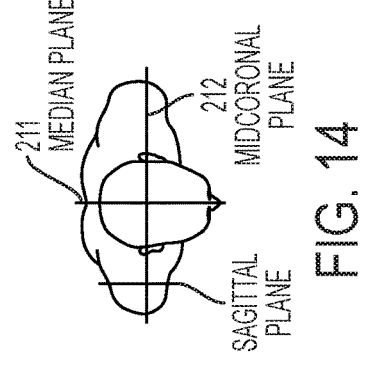
Figure 13:
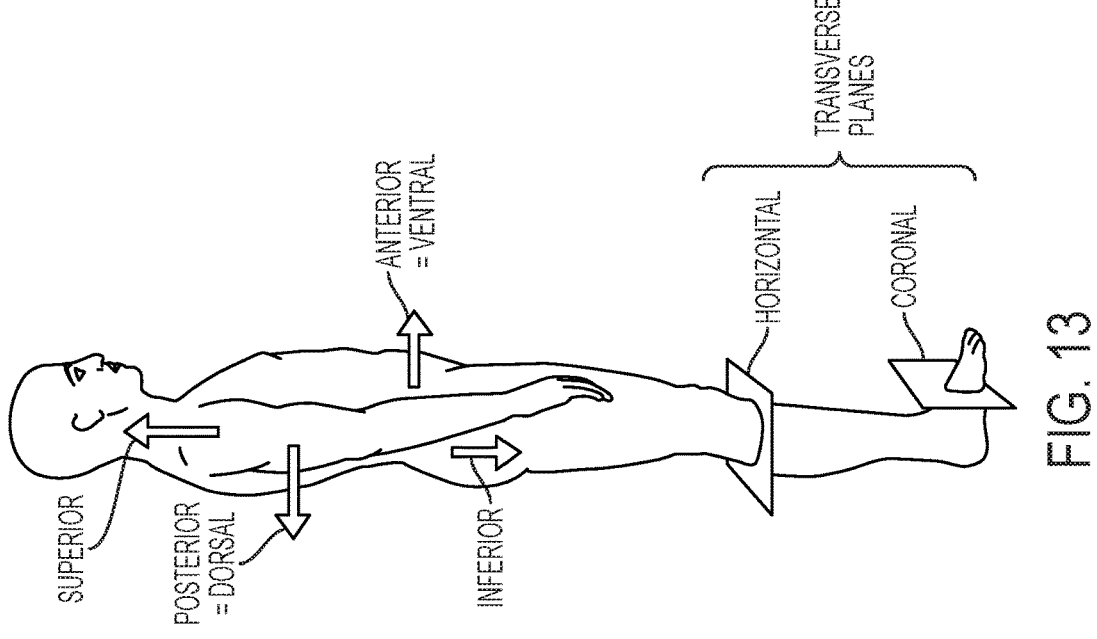

Turning now to the drawings, for example, FIGS. 1-6 and 9 provides schematic illustration of aspects of embodiments of the time-of-flight positron emission tomography (TOF-PET) assembly 301 for detecting lesions of a breast 202 of a subject 201. As an example, the subject 201 is anatomically defined with a medial plane 211 (see FIG. 14) and mid coronal plane 212 (see FIG. 14), and chest wall-coronal plane 204. The detector array 303 may have at least one or more detector segments 304, 305. The detector segments 304, 305 may be configured to acquire tracer emission signals from a target of the breast 202 with a timing resolution of less than about 600 ps, although it is noted that it may be higher The detector segments may be configured to acquire tracer emission signals from a target of the breast with a timing resolution with one or more of any combination of the following ranges:

about 100 ps to about 300 ps;
about 150 ps to about 250 ps;
about 200 ps to about 300 ps;
about 250 ps to about 300 ps;
about 300 to about 600 ps;
about 300 ps to about 400 ps;
about 500 ps to about 600 ps;
about 400 ps to about 500 ps; or
about 400 ps to about 600 ps.

The detector array 303 is configured whereby the detector segments 304, 305 are provided in a ring defining a face substantially spanning across the ring. The ring is being configured to surround the breast 202 and the face of ring is tilted to offset the chest wall-coronal plane 204 of the subject. The tilt is defined by the imaging angle 306 (e.g., detecting angle) between the chest wall-coronal plane 204 and the edge line of response 308, which may be the top of edge 311 of the scintillator. At least one of the top edges 311 of the detector segments 304, 305 is beyond the chest wall-coronal plane 204 of the subject 202 in the posterior direction. The face of ring is tilted to offset the chest wall-coronal plane of the subject. One or more detector segments 304, 305 may be tilted in different alignment (angles) relative to each other compared to the chest wall-coronal plane.

A processor (not shown in FIGS. 1-6 and 9) is configured to receive the acquired tracer emission signals and convert the signals into a three dimensional, tomographic image reconstruction. The detector segments 304, 305 may include (not shown in FIGS. 1-6) a scintillator for placement toward the target, and whereby the scintillator includes a top edge 311 that would be closest to the subject 202. The detector segments 304, 305 may include (not shown in FIGS. 1-6 and 9): a photo multiplier 313 opposite the scintillator 314, and a readout 315 connected to the photo multiplier 313. The detector segments 304, 305 may include (not shown in FIGS. 1-6 and 9) a slant imaging light guide 316 extending from said scintillator 314 to said photo multiplier 313.

The tilt is defined by the detecting angle 306 (e.g., imaging angle) between the chest wall-coronal plane 204 and the edge line of response 308. The detecting angle 306 between the chest wall-coronal plane 204 and the edge line of response 308 may include, but not limited thereto, any one or more of any combination of the following ranges:

about 10 degrees to about 80 degrees;
about 30 degrees to about 60 degrees;
about 40 degrees to about 50 degrees;
about 10 degrees to about 45 degrees; or
about 45 degrees to about 70 degrees.

In an embodiment, the TOFPET assembly may include a top edge 311 of one of the detector segments whereby the tope edge of the detector segment is at least partially under the arm pit of the subject.

Figures 1, 2, 3:
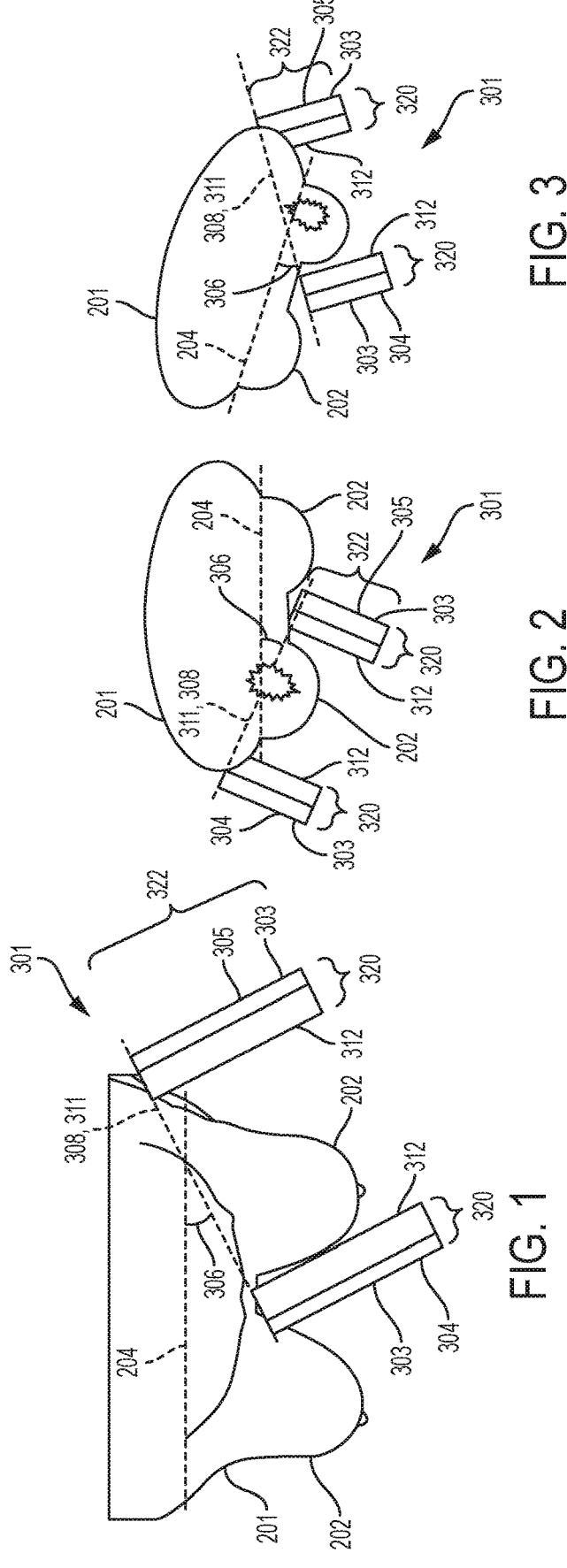
FIG. 1 provides a schematic illustration taken at a horizontal cross-section plane of a subject (left breast) and portion of an embodiment of a time-of-flight positron emission tomography (TOFPET) assembly.
FIG. 2 provides a schematic illustration taken at a horizontal cross-section plane of a subject (right breast) and portion of an embodiment of a time-of-flight positron emission tomography (TOFPET) assembly.
FIG. 3 provides a schematic illustration taken at a horizontal cross-section plane of a subject (left breast) and portion of an embodiment of a time-of-flight positron emission tomography (TOFPET) assembly, whereby relative alignment of subject relative to assembly has been shifted.
Figure 5:
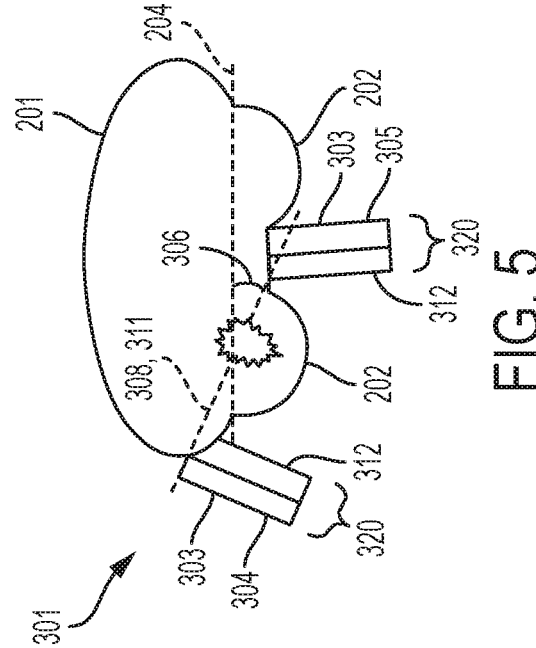
FIG. 5 provides a schematic illustration taken at a horizontal cross-section plane of a subject (right breast) and portion of an embodiment of a time-of-flight positron emission tomography (TOFPET) assembly; similar to FIG. 2 but with the respective alignments of the detection surface walls are in different planes or axes relative to each other.
Figure 4:
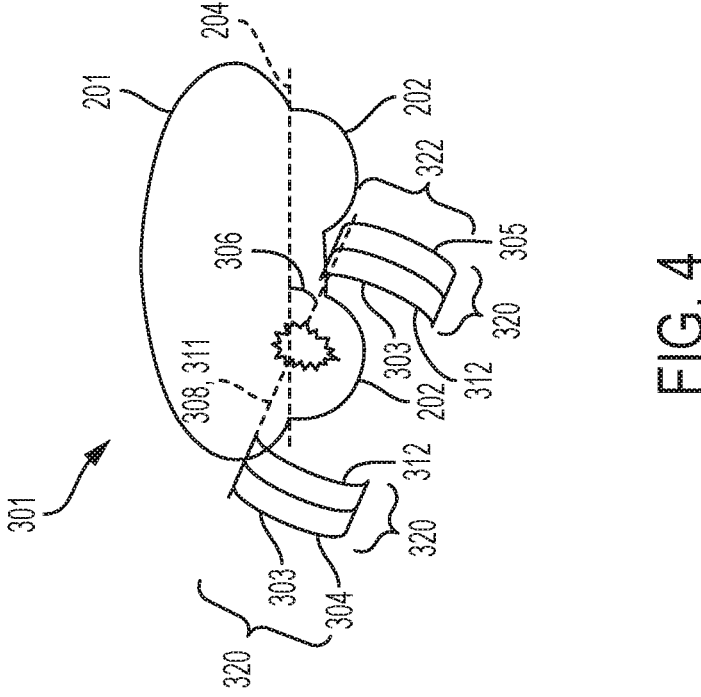
FIG. 4 provides a schematic illustration taken at a horizontal cross-section plane of a subject (right breast) and portion of an embodiment of a time-of-flight positron emission tomography (TOFPET) assembly; similar to FIG. 2 but with the detection surface wall of scintillator being curved.
Figure 6:
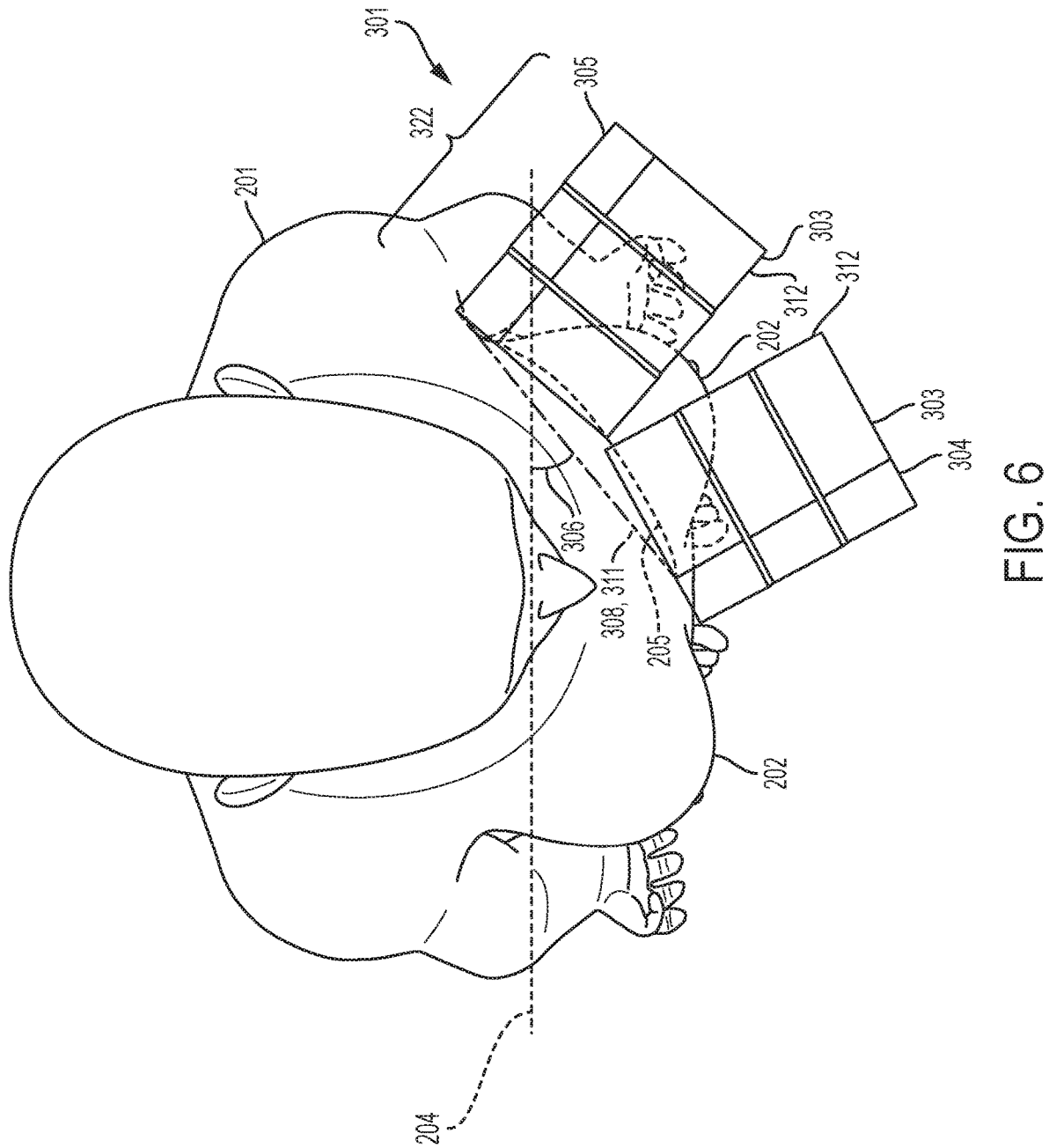
FIG. 6 provides a schematic illustration plan view from the superior of a head of the subject (from above the subject) showing the plan view (above the left and right breasts) and portion of an embodiment of a time-of-flight positron emission tomography (TOFPET) surrounding the left breast.

As shown in FIG. 6, TOFPET assembly may include a top edge 311 of one of the detector segments whereby the tope edge 311 of the detector segment is at least partially beyond of the chest wall-coronal plan 204; and whereby the edge line response 308 is above the edge-of-the-breast 205.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). It is also to be understood that all numbers and fractions thereof are presumed to be modified by the term "about."

Figure 7:
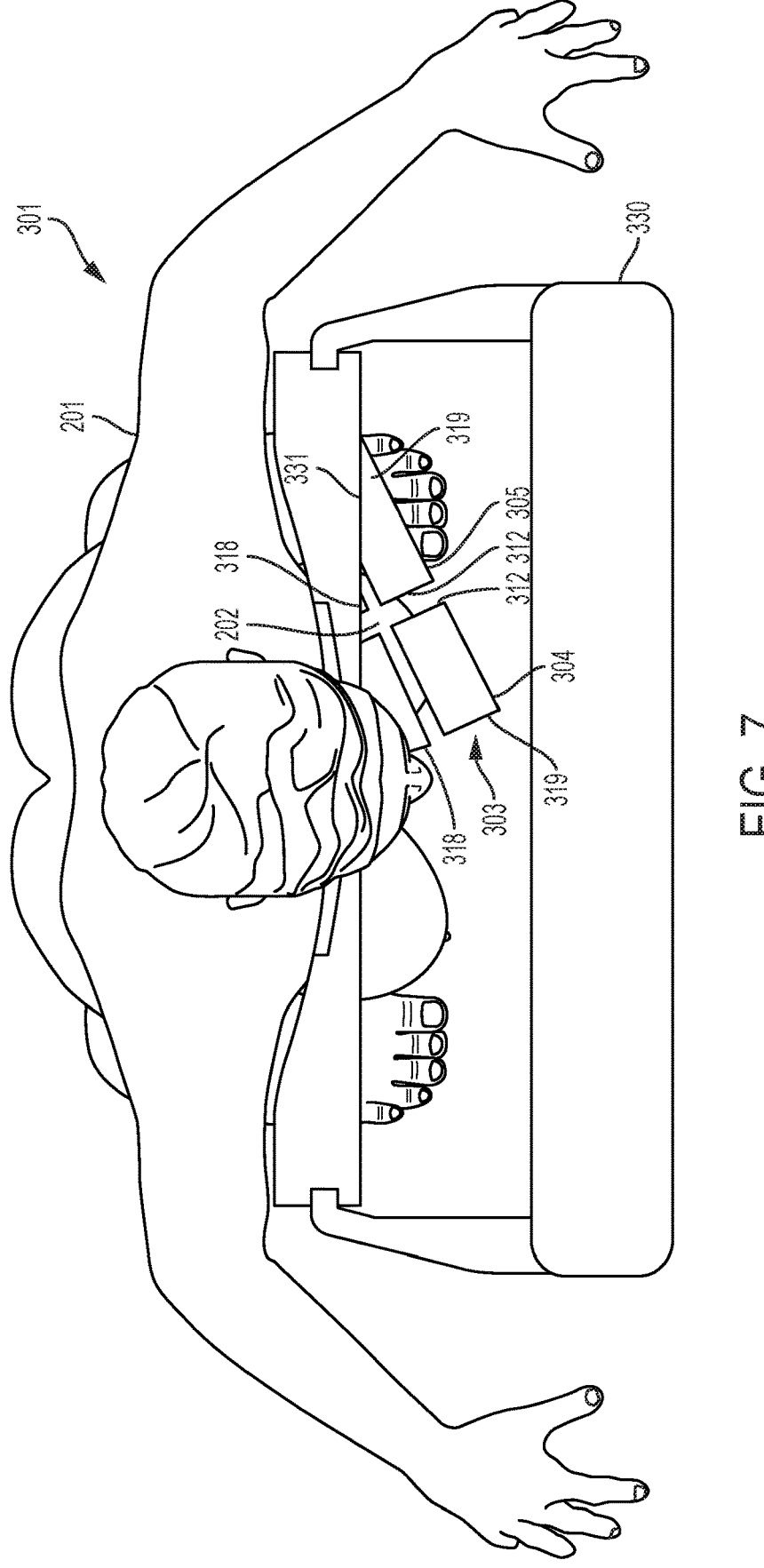
FIG. 7 provides a schematic illustration plan view from the superior of a head of the subject (from above the subject) showing the plan view (above the left and right breasts) and portion of an embodiment of a time-of-flight positron emission tomography (TOFPET) surrounding the left breast; and whereby the subject is positioned in a prone position on a table.
Figure 8:
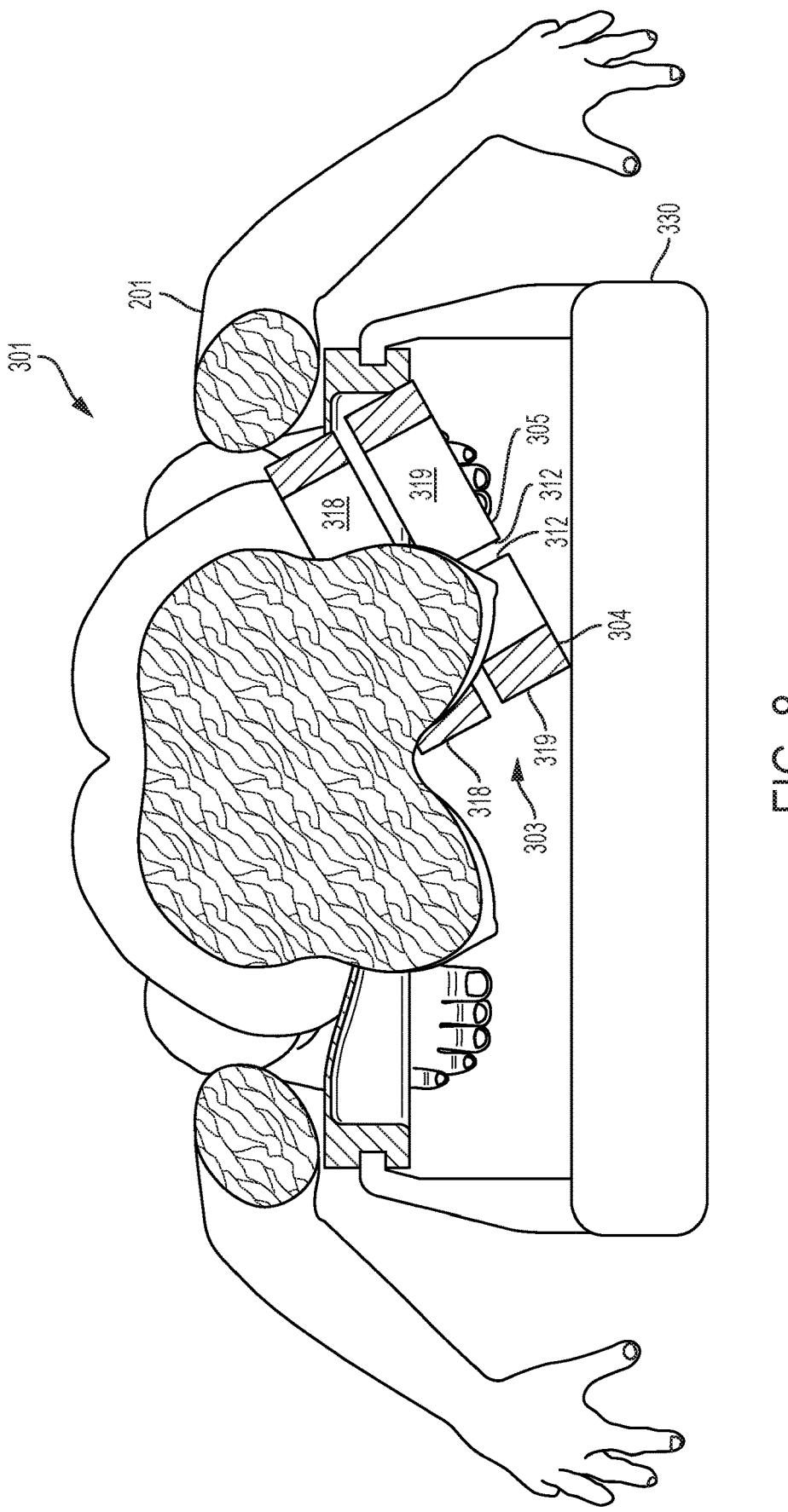
FIG. 8 provides a schematic illustration taken at a horizontal cross-section plane of the subject, table, and portion of an embodiment of a time-of-flight positron emission tomography (TOFPET) assembly. The subjected is positioned in a prone position on the table.
Figure 10:
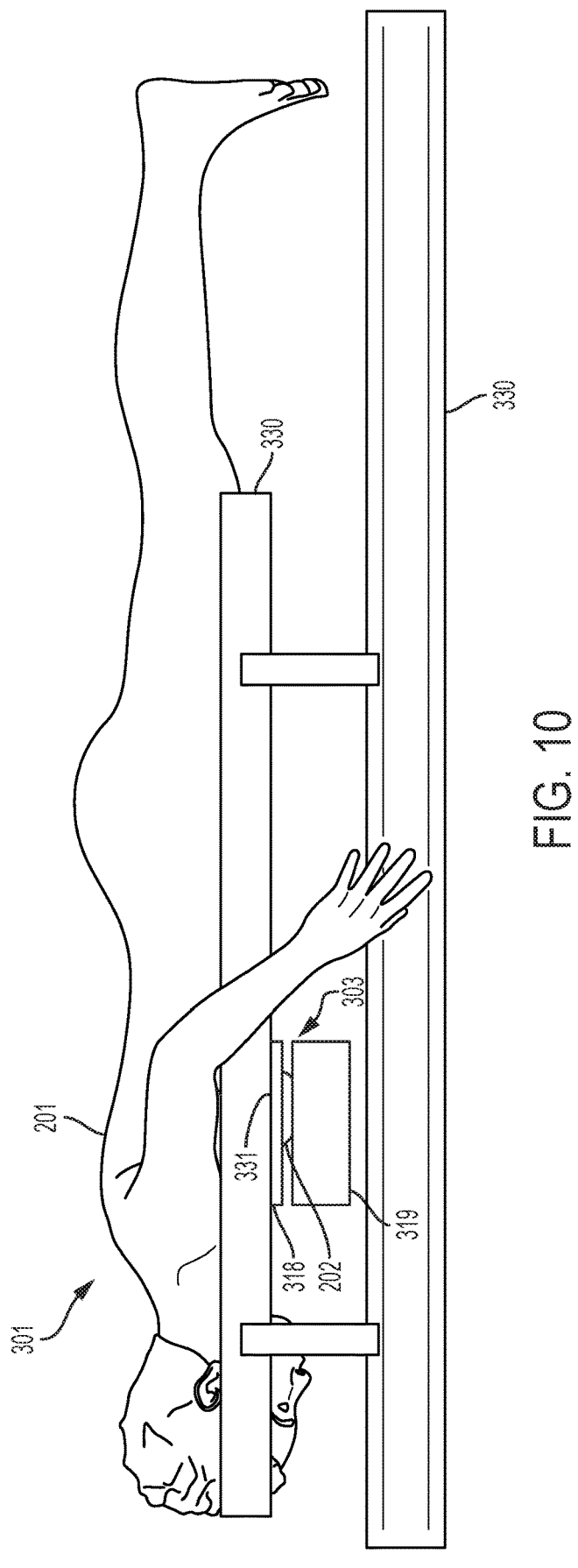
Figure 11:
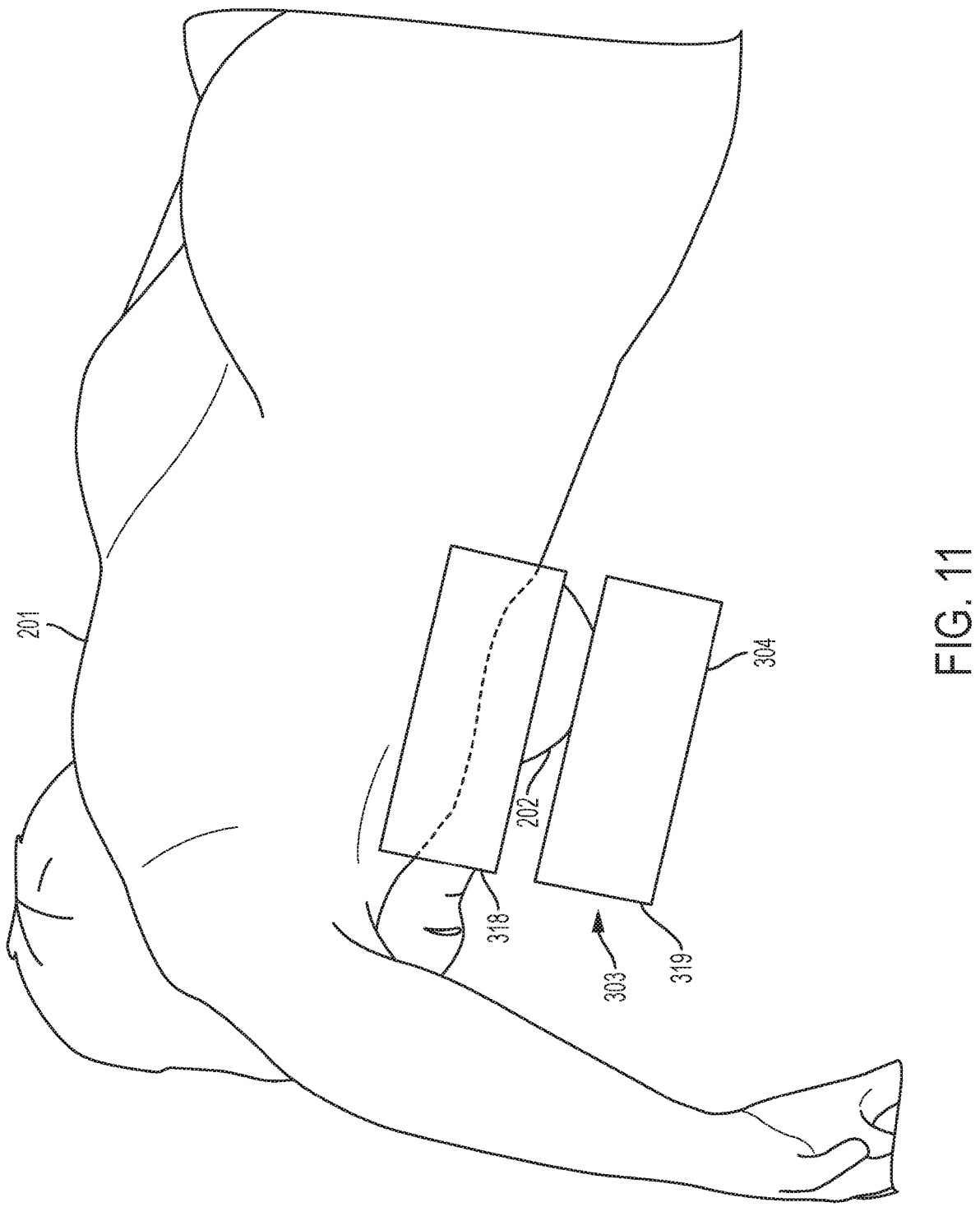
FIG. 11 provides a schematic illustration of a perspective side view from of the subject and portion of an embodiment of a time-of-flight positron emission tomography (TOFPET) surrounding the left breast; and whereby the subject is positioned in a prone position.

As shown in FIGS. 7-8 and 10) The TOFPET assembly 301 may include a table 330 for receiving the subject 202 in the prone position. The table 330 may include a downward extending facing aperture 331 for receiving the breast 202 of the subject 201. As shown in shown FIG. 17, a paddle 332 or tube may be implemented as needed.

In an embodiment the scintillator may comprise scintillator crystals. The scintillator crystals may comprise at least one of any combination of the following: Lutetium Orthosilicate (LSO), Lutetium Yttrium Orthosilicate (LYSO), Lutetium Aluminium Perovskite (LuAP), Lutetium Fine Silicate (LFS), Gadolinium Oxyorthosilicate (GSO), Gadolinium-Yttrium Oxyorthosilicate (GYSO), Bismuth Germanate (BGO), Sodium Iodide (NaI(Tl)), Lanthanum Bromide (LaBr3), or Cerium-Doped Lutetium Yttrium Oxyorthosilicate (Ce:LYSO).

Figure 19:
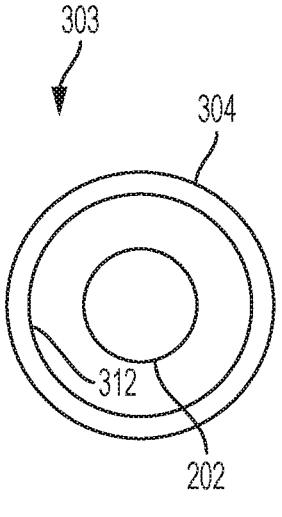
FIG. 19 provides a schematic illustration cross-section side view a detector array to be used for an embodiment of a time-of-flight positron emission tomography (TOFPET) assembly; and whereby the arrays completely surrounds the breast or target.
Figure 20:
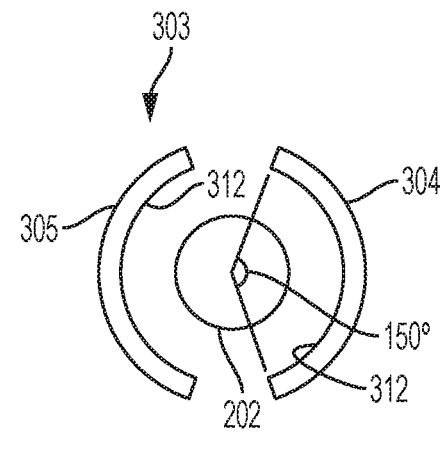
FIG. 20 provides a schematic illustration cross-section side view a detector array having two detector segments to be used for an embodiment of a time-of-flight positron emission tomography (TOFPET) assembly; and whereby the arrays occupy about $\frac{5}{6}$ of a space defining the ring around the breast (150 degrees for each detector segment).
Figure 21:
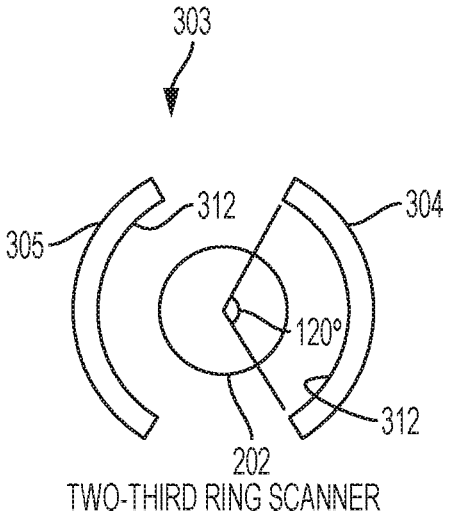
FIG. 21 provides a schematic illustration cross-section side view a detector array having two detector segments to be used for an embodiment of a time-of-flight positron emission tomography (TOFPET) assembly; and whereby the arrays occupy about $\frac{2}{3}$ of a space defining the ring around the breast (120 degrees for each detector segment).
Figure 22:
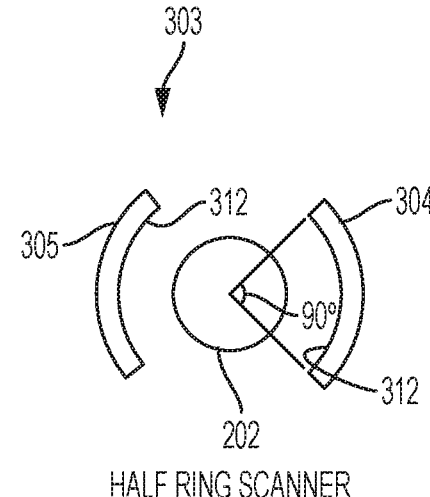
FIG. 22 provides a schematic illustration cross-section side view a detector array having two detector segments to be used for an embodiment of a time-of-flight positron emission tomography (TOFPET) assembly; and whereby the arrays occupy about $\frac{1}{2}$ of a space defining the ring around the breast (90 degrees for each detector segment).

Referring to FIGS. 19-22, the TOFPET assembly that include detector arrays 303 that occupy a variety of space defining the ring around the breast or target. For example, as shown in FIG. 20, the detector segments 304, 305 of the detector array 303 may occupy about ⅚ of a space defining the ring around the breast 202. For example, as shown in FIG. 21, the detector segments 304, 305 of detector array 303 may occupy about ⅔ of a space defining the ring around the breast 202. For example, as shown in FIG. 22, the detector segments 304, 305 of detector array 303 may occupy 50% of a space defining the ring around the breast 202. FIG. 19, a single detector segment 304 of the detector array 303 may occupy the entire space defining the ring around the breast 202. The percent occupancy may vary at a plurality of intervening values including less than 50 percent (half), less than 100 percent (entire).

In an embodiment, detector array 303 may comprise separate detector segments that are either: asymmetrically distributed about a space defining the ring around the breast (or target); or symmetrically distributed about a space defining the ring around the breast (or target).

In an embodiment TOFPET assembly may comprise a photomultiplier that includes at least one of the following: a standard square photomultiplier, a standard round photomultiplier, a multi-element photomultiplier, a position sensitive flat panel photomultiplier, a position sensitive microchannel plate based photomultiplier, a large size avalanche photodiode with resistive readout, and a silicon photomultiplier array.

Figure 16:
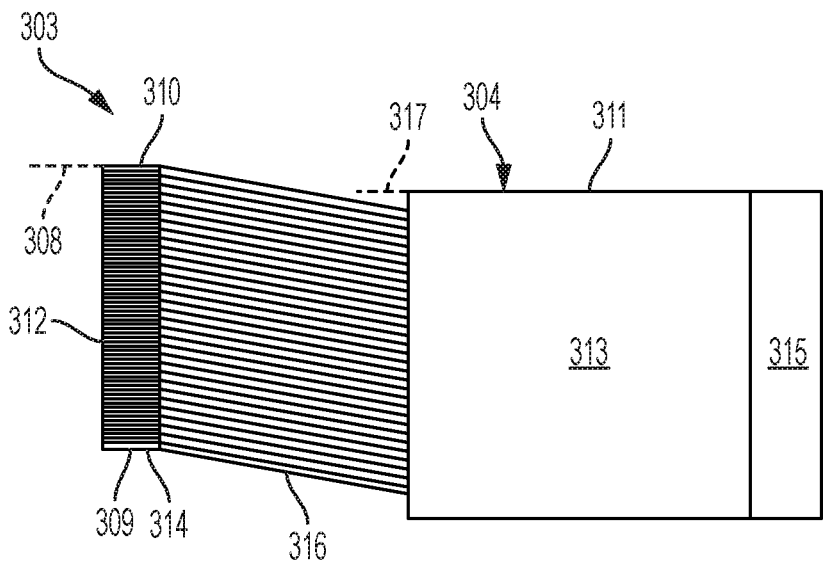
FIG. 16 provides a schematic illustration cross-section side view a detector array to be used for an embodiment of a time-of-flight positron emission tomography (TOFPET) assembly.
Figure 17:
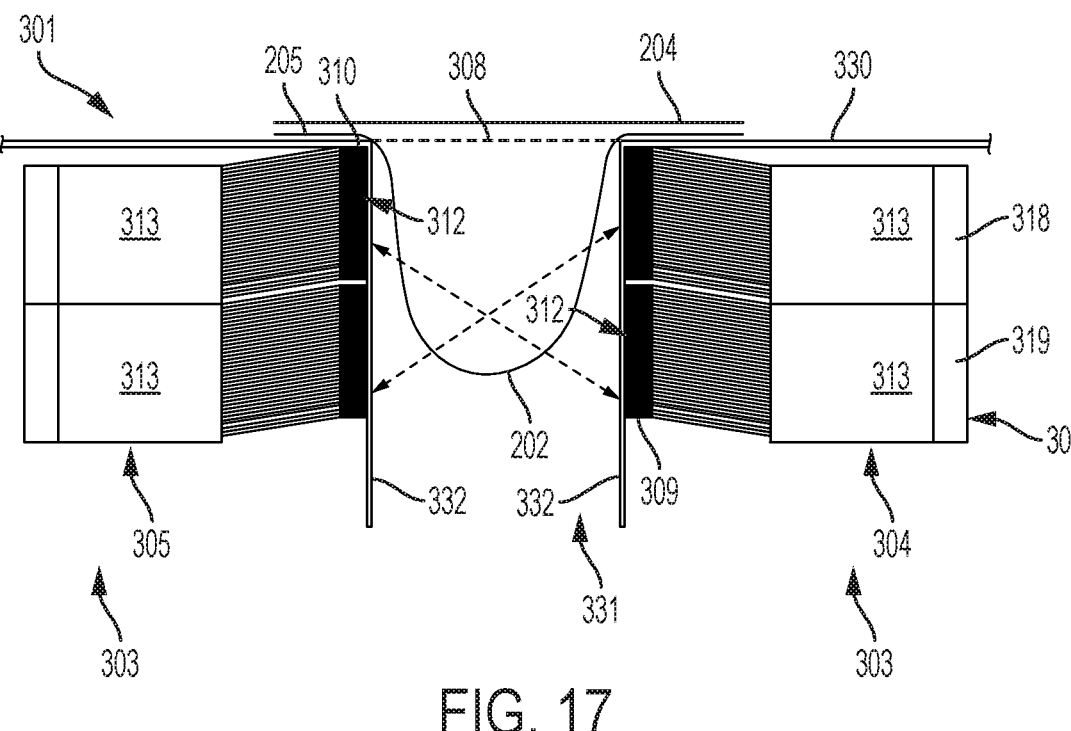
FIG. 17 provides a schematic illustration cross-section side view two detector arrays (having an inner and outer ring) to be used for an embodiment of a time-of-flight positron emission tomography (TOFPET) assembly; and whereby the arrays are not yet in position for operation.
Figure 18:
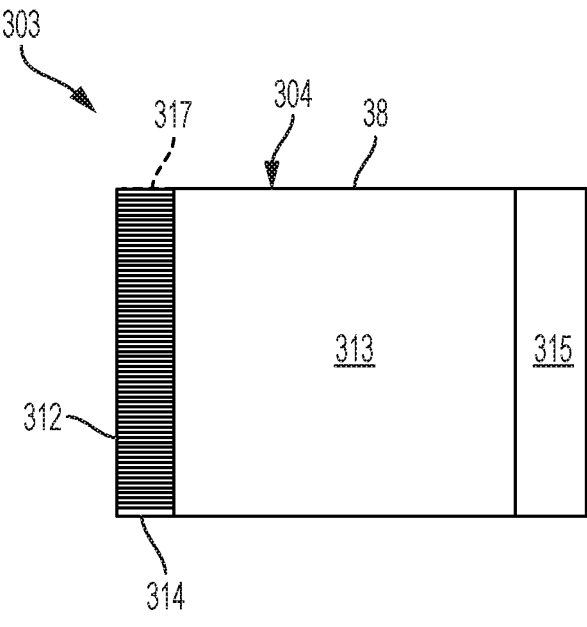
FIG. 18 provides a schematic illustration cross-section side view a detector array to be used for an embodiment of a time-of-flight positron emission tomography (TOFPET) assembly; and which excludes a light guide.

Turning now to the drawings, for example, FIGS. 16-18 provides schematic illustration (cross-section side views) of aspects of embodiments of the time-of-flight positron emission tomography (TOFPET) assembly 301 for detecting lesions of a breast 202 of a subject 201. FIG. 16 includes a detector array 303 showing a portion of a detector segment 304 that provides the scintillator 314 in communication with the slant imaging light guide 316, photomultiplier 313, and readout 315. Also shown is the edge line response 308 of scintillator 314 and plane or surface 317 defining top edge of photomultiplier. Also shown is a top edge 310 and bottom edge 309 of a detector segment 304 (particularly the scintillator 314). Also shown is the detection surface wall 312 of scintillator 314.

FIG. 17 provides an embodiment of the time-of-flight positron emission tomography (TOFPET) assembly 301 that includes the portion of the illustration similar to FIG. 16, with the addition of including not just an inner imaging row 318 but also an outer imaging row 319. The breast 202 of the subject is shown disposed through an aperture 331 of the table 330 assuming the subject is positioned on the table 330 in a prone position. The detector array 303 is not yet placed in operating condition/position as the edge line response 308 is below the edge of the breast 205 and the edge line response 308 is also below the chest-wall-coronal plane 204. Similarly, the top edge of the detector segment 310 is still below the edge of the breast 205 and chest wall-coronal plane 204 (since the detector array 303 is not yet placed in operating condition/position). Also shown is the detection surface wall 312 of scintillator 314. Also shown is a paddle 332 or tube may be implemented as needed.

FIG. 18 includes a detector array 303 showing a portion of a detector segment 304 similar to as shown in FIG. 16, but without a light guide. The scintillator 314 is in communication with the photomultiplier 313 and readout 315. Also shown is the detection surface wall 312 of scintillator 314.

Turning now to the drawings, for example, FIGS. 7-8 and 10 provides schematic illustration of aspects of embodiments of the time-of-flight positron emission tomography (TOFPET) assembly 301 for detecting lesions of a breast 202 of a subject 201, and whereby the subject 201 is positioned in a prone position on a table 330. The detector array 303 may have at least one or more detector segments 304, 305. The detector segments 304, 305 may be configured to acquire tracer emission signals from a target of the breast 202. The detector array 303 may have at least one or more rings, such as an inner ring 318 and an outer ring 319. Also shown is the detection surface wall 312 of detector segments 304, 305 of FIGS. 7-8.

Figure 9:
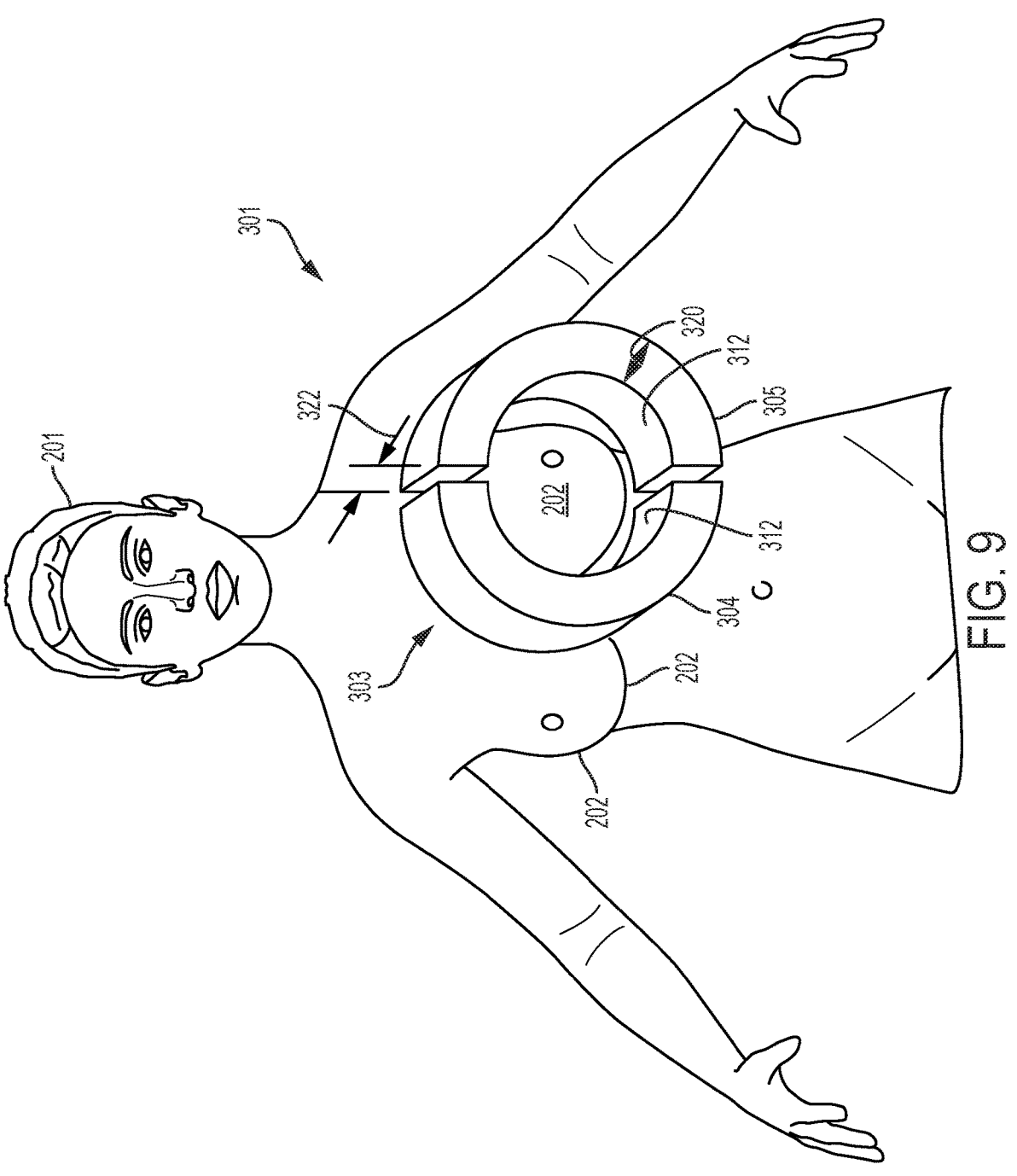
FIG. 9 provides a schematic illustration side view from the anterior of the subject showing the anterior view and portion of an embodiment of a time-of-flight positron emission tomography (TOFPET) assembly surrounding the left breast FIG. 10 provides a schematic illustration side view from of the subject and portion of an embodiment of a time-of-flight positron emission tomography (TOFPET) surrounding the left breast; and whereby the subject is positioned in a prone position on a table.

Turning now to the drawings, for example, FIG. 9 provides a schematic illustration of an aspect of embodiment of the time-of-flight positron emission tomography (TOFPET) assembly 301 for detecting lesions of a breast 202 of a subject 201. The detector array 303 may have at least one or more detector segments 304, 305. The detector segments 304, 305 may be configured to acquire tracer emission signals from a target of the breast 202. The detector segments 304, 305 may have a width (thickness) 320 that may vary. Also, the detector segments 304, 305 may have a depth 322 that varies thus varying the depth or surface of the detection surface wall 312 of the scintillator of the array.

Figure 12:
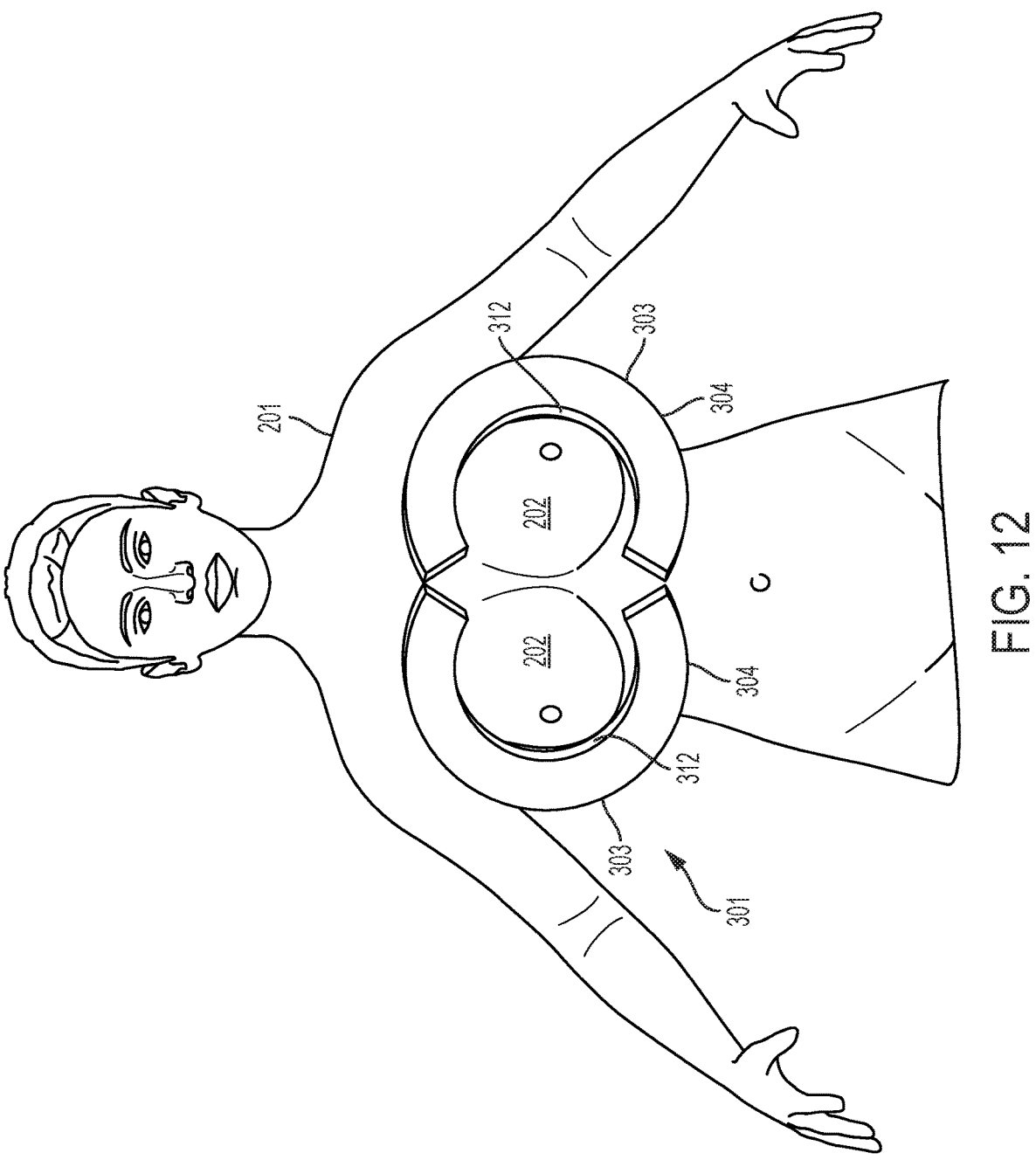
FIG. 12 provides a schematic illustration side view from the anterior of the subject showing the anterior view and portion of an embodiment of a time-of-flight positron emission tomography (TOFPET) assembly at least partially surrounding the left breast and the right breast.
Figure 15:
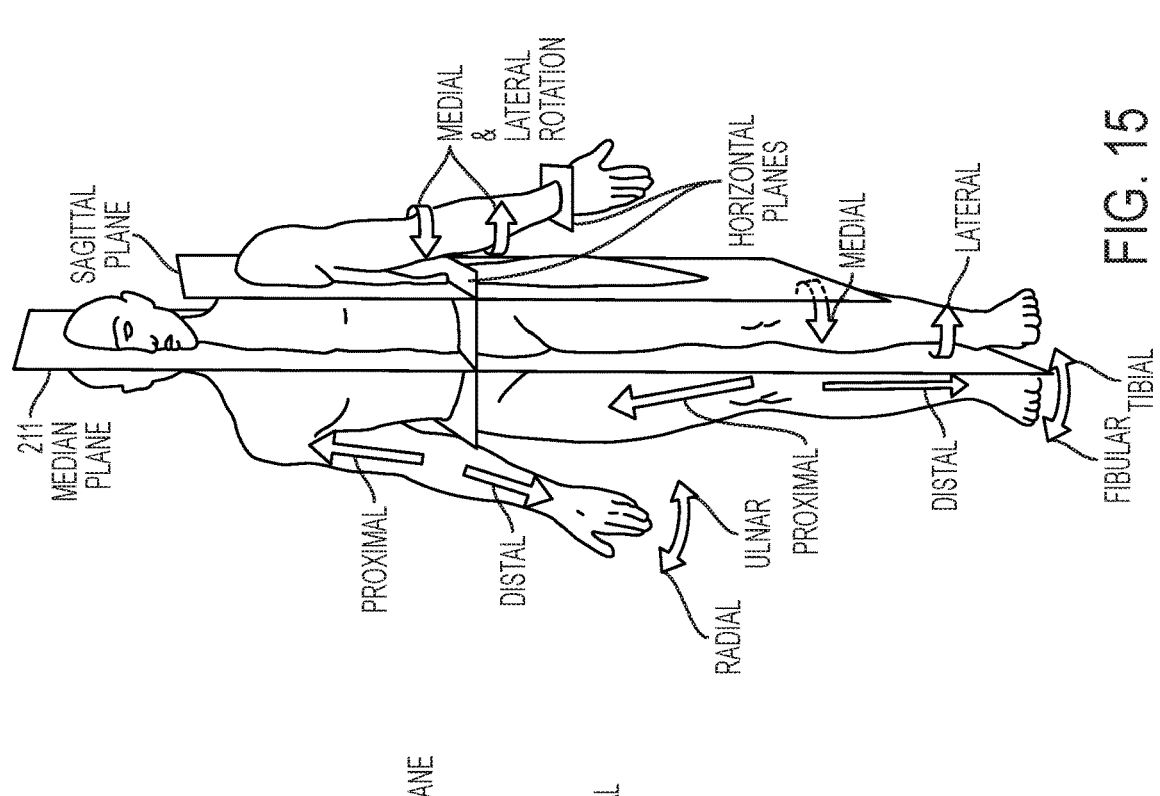
FIGS. 13-15 provides a schematic illustration showing the chief terms of position and direction and the main planes of reference in the body of a subject.

Turning now to the drawings, for example, FIG. 12 provides a schematic illustration of an aspect of embodiment of the time-of-flight positron emission tomography (TOFPET) assembly 301 for detecting lesions of a breast 202 of a subject 201. The detector array 303 includes only a single detector segment 304 for each array 303 for each breast 202 (i.e., the left and right breasts). It is noted that while detector array 303 includes only a single detector segment 304 there may be more than one ring, such as inner imaging ring 318 (not shown) and outer imaging ring 319 (not shown).

Figure 23:
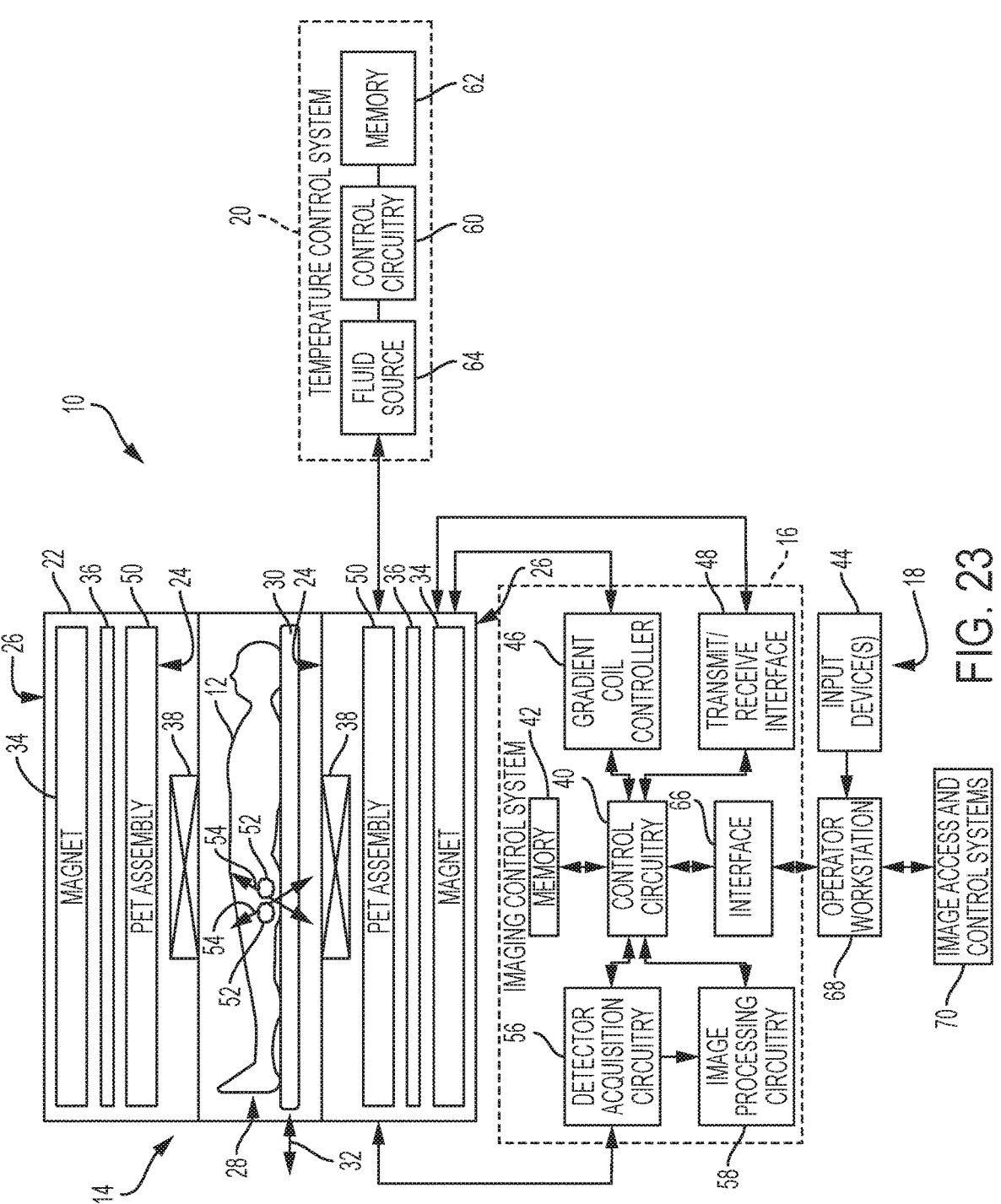
FIG. 23 provides a schematic illustration an embodiment of a time-of-flight positron emission tomography (TOFPET) assembly for an imaging system.

Turning now to the drawings, FIG. 23 diagrammatically illustrates an imaging system 10 for imaging a subject 12. However, the depiction of a subject (e.g., a patient) is merely an example. The subject 12 may be any target object, any, human, and so forth, in other embodiments. The imaging system 10 includes an imaging device 14, an imaging control system 16, a health care facility system 18, and a temperature control system 20. During operation, the imaging device 14 may be configured to image the subject 12 (e.g., patient) via one or more imaging modalities under control of the control system 16. The control system 16 may receive one or more inputs from the health care facility system 18 regarding operation of the device and output data related to imaging of the patient 12. The temperature control system 20 may coordinate with the control system 16 to facilitate cooling of one or more components of the imaging device 14 during operation.

In the illustrated embodiment, the imaging device 14 includes a frame 22 having an inner transaxial wall 24 and an outer transaxial wall 26. The inner transaxial wall 24 may define a transaxially extending bore 28 configured to receive a patient support 30. The patient support 30 may be configured to position the patient 12 within the transaxially extending bore 28, for example, via movement of the patient support 30 within, or into and out of, the frame 22, as indicated by arrow 32.

In the illustrated embodiment, the imaging system 10 may be a combined PET and MRI imaging system. However, it should be noted that in other embodiments, the imaging system 10 may combine PET with any other suitable imaging modality, such as X-ray CT or ultrasound. Indeed, the depicted MRI/PET system is merely an example.

In the depicted embodiment, the imaging device 14 includes components suitable for performing both MRI and PET. Specifically, the MRI portion of the device 14 may include a magnet 34 configured to generate a primary magnetic field. In some embodiments, the magnet 34 may be driven by a power source (not shown) provided, for example, by control system 16. One or more gradient coils 36 may be configured to generate magnetic gradient fields during imaging. A radio frequency (RF) coil 38 may generate RF pulses for exciting the nuclear spins and/or function as a receiving coil, depending on the given implementation. The arrangement of the magnet 34, the one or more gradient coils 36, and the RF coil 38 is subject to a variety of implementation-specific variations. However, in the illustrated example, the RF coil 38 is nested within the one or more gradient coils 36, which are nested within the magnet 34.

Centralized control circuitry 40 may control both the MRI and PET subsystems of the imaging system 10. With respect to the MRI sub-system, the control circuitry 40 may control the MRI components to generate a desired magnetic field and RF pulses and to process the generated signals. To that end, the control circuitry 40 may include one or more processors communicatively coupled to memory 42. The one or more processors (e.g., microprocessor(s), application-specific integrated circuit (ASIC), field-programmable gate array (FPGA), etc.) may be configured to execute a control algorithm. By way of example, the control algorithm may be provided as machine-readable encoded instructions stored on a machine-readable medium, such as the memory 42, and may provide control signals for controlling operation of the imaging system 10. The control signals may control the imaging device 14 to selectively acquire MRI and/or PET data.

The memory 42 may be a tangible, non-transitory, machine readable medium. For example, the memory 42 may be volatile or non-volatile memory, such as read only memory (ROM), random access memory (RAM), magnetic storage memory, optical storage memory, or a combination thereof. Furthermore, a variety of control parameters may be stored in the memory 42 along with code configured to provide a specific output (e.g., enable MRI image acquisition, enable PET image acquisition, etc.) to the imaging device 14 during operation. The memory 42 may also store acquired image data, pulse sequences for different modes of operation, or any other parameters defining examination sequences performed by the MRI portion of the device 14. Further, in some embodiments, the processor(s) of the control circuitry 40 may also receive one or more inputs from one or more input devices 44, through which the user may choose a process and/or input desired parameters (e.g., which part of the body should be imaged, whether multiple or single modality operation is desired, etc.).

In some embodiments, a gradient coil controller 46 and a transmit/receive interface 48 may provide interfaces through which the control circuitry 40 may control the one or more gradient coils 36 and RF coil 38. For example, the gradient coil controller 46 may include amplification circuitry configured to drive current for the one or more gradient coils 36 under control of circuitry 40. For further example, the transmit/receive interface 48 may include amplification circuitry to drive the RF coil 38 during operation. In some embodiments, the RF coil 38 may be configured to both emit RF excitation pulses and receive responsive signals, and the transmit/receive interface 48 may include a switch configured to toggle the RF coil 38 between transmit and receive modes of operation.

In addition to the MRI subsystem, the imaging device 14 also includes one or more components that enable PET imaging. For example, a PET assembly 50 is disposed between the inner transaxial wall 24 and the outer transaxial wall 26 of the frame 22 of the imaging device 14. In the illustrated embodiment, the PET assembly 50 is disposed annularly between the one or more gradient coils 36 and the RF coil 38. However, in other embodiments, the PET assembly 50 may be disposed in any other desired location within the frame 22.

Further, although the PET assembly 50 is illustrated as an integrative part of the frame 22 in the illustrated example, the PET assembly 50 may be configured as a removable insert in other embodiments. For example, the PET assembly 50 may be provided as part of a retrofit kit configured to retrofit an existing imaging system (e.g., MRI system or CT system) to endow the existing system with PET imaging capabilities. Such a retrofit kit may include the PET assembly 50 configured to be inserted into an existing frame 22 and/or software configured to be executed by the control circuitry 40 to enable control of the PET assembly and/or processing of the acquired data.

The PET assembly 50 may include an annular scintillation crystal coupled to one or more photodetectors, as discussed in more detail below, to enable the PET assembly 50 to function as a PET detector. To that end, the patient 12 may be administered a positron-emitting source 52 which will result in the production of a pair of gammas. In some embodiments, the PET subsystem may generate images illustrating the distributions of positron-emitting nuclides in the patient 12. To that end, the PET assembly 50 may operate on the principle of annihilation coincidence detection (ACD). In such embodiments, a positron is emitted by a nuclear transformation of a radiopharmaceutical (e.g., radiation source 52), and the positron annihilates with an electron to result in photons 54 emitted in opposite directions and detected by PET assembly 50. The single crystal scintillator in the PET assembly 50 may detect the photons 54 and produce visible photons detectable by photodetectors.

Detector acquisition circuitry 56 may be configured to control acquisition of the signals acquired by the PET assembly 50 in coordination with central control circuitry 40. Image processing circuitry 58 may process the acquired data from the detector acquisition circuitry 56. For example, the image processing circuitry 58 may include one or more processors configured to receive the PET image data and the MRI image data, and to overlay the PET data over the MRI data to generate a composite image.

In the illustrated embodiment, the centralized control circuitry 40 controls the PET and MRI subsystems of the imaging system 10. To that end, the control of the subsystems is coordinated to enable acquisition of PET and MRI data while the patient 12 is in the same position. The foregoing feature may offer the advantage of enabling reduction in imaging acquisition time (e.g., because the patient does not have to be moved between imaging modalities) and/or reduction in image artifacts due to patient movement.

In some embodiments, the temperature control system 20 may also be under control of the control circuitry 40 to enable cooling of one or more components of the imaging device 14. For example, the temperature control system 20 may include control circuitry 60 (e.g., one or more processors) communicatively coupled to control circuitry 40. The control circuitry 60 may access memory 62 (which may include components similar to memory 42 described above) to facilitate control of a fluid source. For example, the control circuitry 60 may control a pump to pump fluid from the fluid source 64 to one or more tubes in the PET assembly 50 to cool one or more components in the PET assembly 50, as described in more detail below.

Further, the imaging control system 16 may include one or more devices that facilitate interaction between a user and the imaging device 14. For example, an interface 66 may communicatively couple the control circuitry 40 to an operator workstation 68. The operator workstation 68 may be a general purpose or special computer including, for example, memory for storing pulse sequences, examination protocols, patient data, raw and/or processed image data, and so forth. The operator workstation 68 may receive one or more operator inputs via the user input devices 44. The user input devices 44 may include, but are not limited to, mobile devices (e.g., smartphones, tablets, laptops, etc.), keyboards, computer mice, etc. The operator workstation 68 may also be coupled to one or more local or remote image access and control systems 70, such as picture archiving and communication systems (PACS), teleradiography systems (TELERAD), etc.

Figure 24:
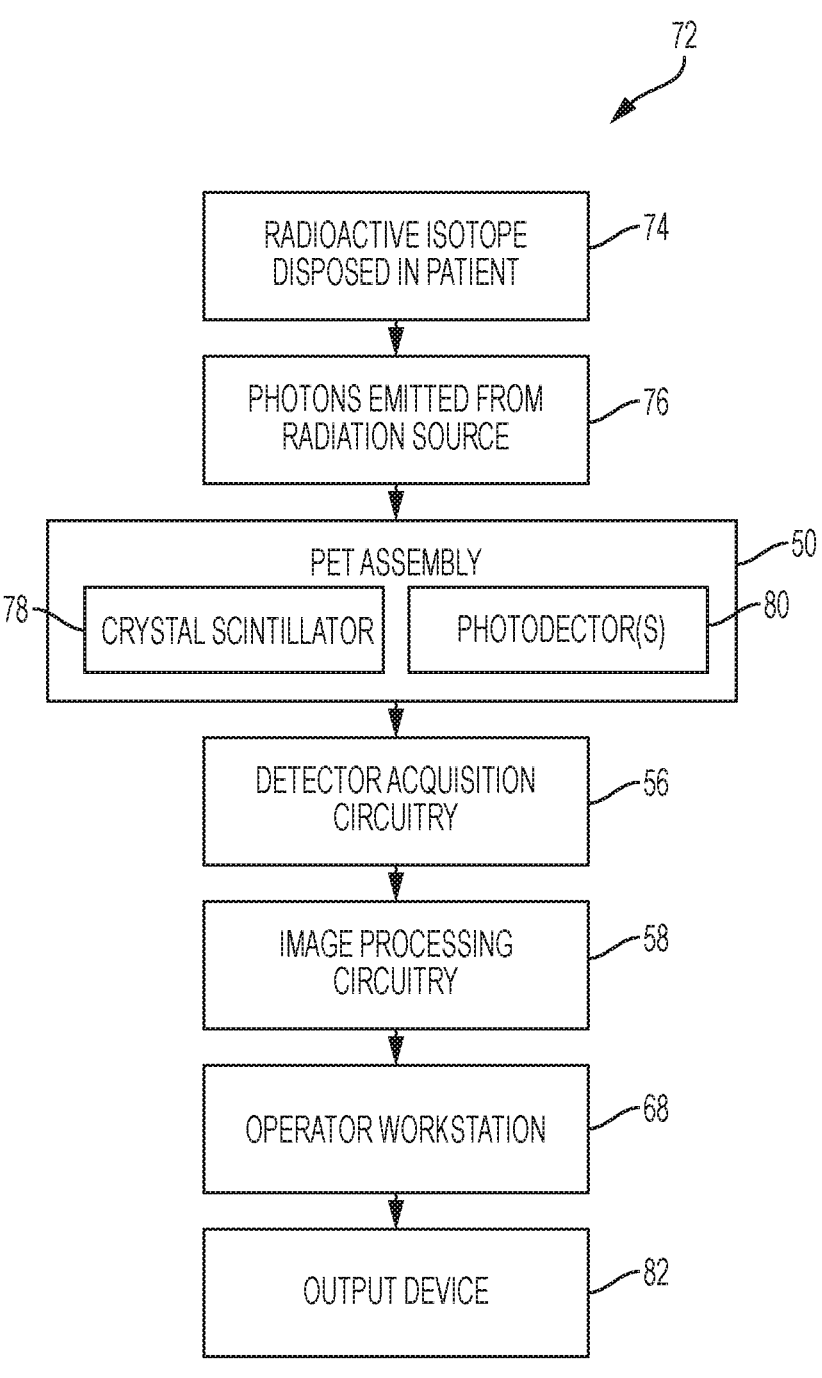
FIG. 24 provides a flow chart for the technique for using an embodiment of a time-of-flight positron emission tomography (TOFPET) assembly for an imaging system.

FIG. 24 illustrates an embodiment for a technique and method for using a standalone PET imaging system 72 in accordance with a disclosed embodiment. That is, in this embodiment, the PET assembly 50 may form an integral or removably insertable part of a single modality system 72. As shown, in this embodiment, a radioactive isotope (e.g., radiation source 52) is disposed in the patient 12 (block 74). In some embodiments, the radioactive isotope may be targeted to a desired location(s) within the patient 12 by chemically binding it to a targeting ligand, such glucose, a peptide, small molecule, etc. Photons are emitted from the radioactive isotope 52 (block 76) and detected by one or more detection elements of the PET assembly 50.

In the illustrated embodiment, the PET assembly 50 includes a scintillator crystal 78. The crystal 78 may be formed in a variety of suitable shapes.

The crystal scintillator 78 may be formed from any suitable material. For example, the crystal 78 may include, but is not limited to, LYSO (Cerium-doped Lutetium Yttrium Orthosilicate), $LaBr_3$ (Lanthanum Bromide), NaI (Tl) (Sodium Iodide), BGO (Bismuth Germanate), a combination thereof, or any other suitable scintillator material. The scintillator 78 may be a dense material capable of converting a highly energy gamma ray (e.g., 511 keV in the case of positron emitters), and lower energy in the case of single gamma emitters, such as, but not limited to, $^{99m}Tc$, and $^{111}In$) into visible light. The visible light may be detected by one or more photodetectors 80. The one or more photodetectors 80, may include, but are not limited to, avalanche photo diodes, silicon photomultipliers (SiPMs), or any other suitable photodetector.

In the PET system 72, the PET assembly 50 is under control of the detector acquisition circuitry 56, as described above. Further, the image processing circuitry 58 is communicatively coupled to the detector acquisition circuitry 56 to receive and process the PET image data, as described in detail above. Likewise, the operator workstation 68 may be included in the PET system 72 to enable operator input. Additionally, an output device 82, such as a display or printer, may be configured to output the PET images generated during operation of the PET imaging system 72.

Figure 25:
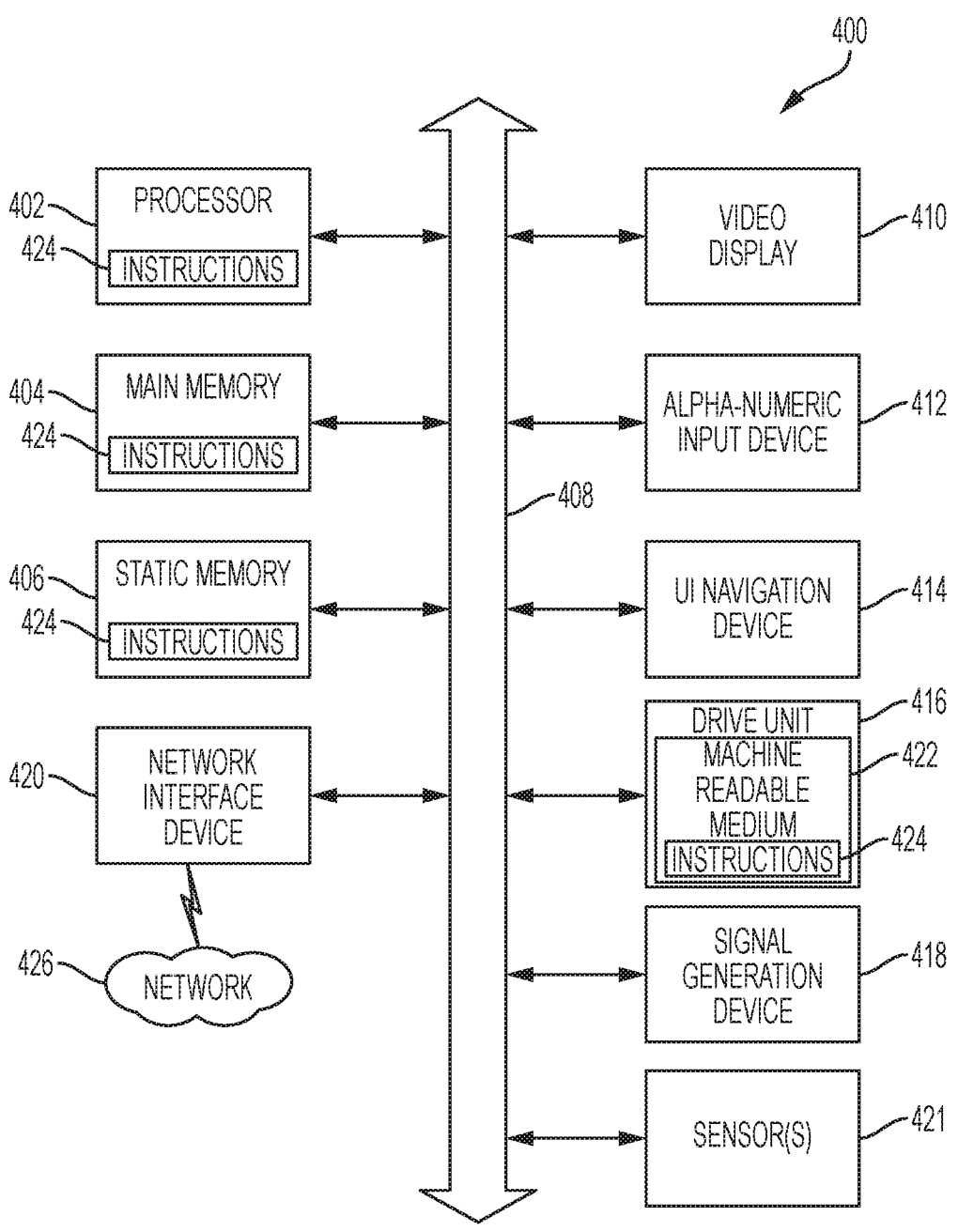
FIG. 25 illustrates a block diagram of an example machine 400 upon which one or more embodiments (e.g., discussed methodologies) can be implemented (e.g., run).

FIG. 25 is a block diagram illustrating an example of a machine upon which one or more aspects of embodiments of the present invention can be implemented.

FIG. 25 illustrates a block diagram of an example machine 400 upon which one or more embodiments (e.g., discussed methodologies) can be implemented (e.g., run).

Examples of machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a nontransitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a stand-alone device or the machine 400 can be connected (e.g., networked) to other machines.

In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410, an alphanumeric input device 412 (e.g., a keyboard), and a user interface (UI) navigation device 411 (e.g., a mouse). In an example, the display unit 410, input device 412 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

Any of the components or modules referred to with regards to any of the present invention embodiments of the device discussed herein, may be integrally or separately formed with one another. Further, redundant functions or structures of the components or modules may be implemented.

Any of the components or modules may be a variety of widths and lengths as desired or required for operational purposes.

It should be appreciated that various sizes, dimensions, contours, rigidity, shapes, flexibility and materials of any of the components or portions of components in the various embodiments of the device discussed throughout may be varied and utilized as desired or required. Similarly, locations and alignments of the various components may vary as desired or required. Moreover, modes and mechanisms for connectivity or interchangeability may vary.

It should be appreciated that the device and related components of the device discussed herein may take on all shapes along the entire continual geometric spectrum of manipulation of x, y and z planes to provide and meet the environmental, and structural demands and operational requirements. Moreover, locations, connections and alignments of the various components may vary as desired or required.

EXAMPLES

Practice of an aspect of an embodiment (or embodiments) of the invention will be still more fully understood from the following examples and experimental results, which are presented herein for illustration only and should not be construed as limiting the invention in any way.

A short summary of conceptual and technical aspects of the overall novel approach and system (which is not intended to be an exhaustive list of features) is provided below:

the two opposite detector sectors having either regular form (example: sectors of a cylinder) or irregular form (arrangement of individual detector modules) are placed in a tilted geometry at about orthogonal direction to the axis of the patient to allow for high PET visibility of the base of the breast.

the sizes of the modules are sufficiently large to view the whole breast in one static position of the detector (no scanning) to enable dynamic data recording and kinetic model analysis of the uptake and washout of the PET imaging agent simultaneously in the whole breast.

to allow for such an arrangement the detector modules use very compact (thin) detector module design composed of high stopping power, bright and fast crystal scintillators such as LSO, LYSO, LGSO, etc. coupled to fast photo detector modules made of very compact solid state technology-Silicon Photomultipliers (SiPMs); the scintillator modules can be in the form of monolithic plates or pixellated arrays, or vertical combinations of several monolithic or pixellated scintillation blocks.

to further minimize the distance from the active detector edge to the chest wall compact light guides are introduced between the scintillator gamma sensor and the photodetector SiPM sensor.

further, SiPMs are mounted on printed circuit readout boards with very compact accompanying front-end circuitry.

the remainder of the readout (such as signal shaping or conditioning, digitizing, coincidence circuitry, etc.) is mounted in separate boxes connected by compact low-profile cables; this additional electronics can be for example mounted under the patient bed or in a separate mobile cabinet.

the detector is made Time of Flight (TOF) capable to minimize or eliminate the non-uniformity of the response (that results in presence of artifacts in reconstructed tomographic images) due to the limited angle geometry of the system (missing angular coverage in the directions up and down from the breast, relative to the patient's body axis); the desired TOF resolution is less than 350 psec. FWHM, preferably in the 150-250 psec. range.

the patient table has top surface optimized for close positioning of the PET detector sectors or modules at the patient's curved body.

in the basic approach the coincident dynamic event data of only one preselected breast (option with two simultaneously breasts covered is also possible) are recorded in a list mode with a fast TOF-compatible time flag and/or using fast coincidence circuitry; the data are recorded from the moment of injection to the defined end point of scanning; second breast is imaged in a standard static mode.

a simultaneous dynamic two-breast option is also considered providing more direct comparison of the two breasts being scanned simultaneously, however potentially at an increased hardware and software complexity and at higher cost.

attenuation of the photons in the breast(s) is compensated using iterative TOF reconstruction; in this emission and attenuation can be estimated. Scatter correction will be made feasible with this approach.

The present inventors submit that in at least some instances, simultaneous imaging of the two breasts may be actually overall more economical because, among other things:

one would reduce time (=cost) by half (or more considering decay time) so eventually one can increase scanner throughput.

one can be able to scan also C-11 tracers with only one injection (time, cost).

Additional Examples

Practice of an aspect of an embodiment (or embodiments) of the invention will be still more fully understood from the following examples and experimental results, which are presented herein for illustration only and should not be construed as limiting the invention in any way.

Example 1. An aspect of an embodiment of the present invention provides, among other things, a time-of-flight positron emission tomography (TOFPET) assembly for detecting lesions of a breast of a subject, wherein the subject may anatomically be defined with a median plane and chest wall-coronal plane. The assembly may comprise: a detector array having at least two or more detector segments. The detector segments may include: a scintillator for placement toward the target, the scintillator having a top edge generally closest to the subject and a detection surface wall aligned closest to surrounding the breast, a photo multiplier opposite the scintillator, and a readout connected to the photo multiplier. The detector segments may be configured to acquire tracer emission signals from a target of the breast with a timing resolution of less than about 600 ps. The assembly may also comprise a processor that receives the acquired tracer emission signals and converts the signals into a three dimensional, tomographic image reconstruction. The detector array may be configured having the at least two segments in a ring defining a face substantially spanning across the ring. Further, the ring surrounding the breast and the face of ring may be tilted to offset the chest wall-coronal plane of the subject; and wherein one of the top edge of one of the detector segments is above the chest wall-coronal plane of the subject in the posterior direction.

Example 2. The TOFPET assembly of example 1, further comprising a slant imaging light guide extending from said scintillator to said photo multiplier.

Example 3. The TOFPET assembly of example 1 (as well as subject matter in whole or in part of example 2), wherein the angle between the face of the ring and the chest wall-coronal plane is in the range of about 10 degrees to about 80 degrees.

Example 4. The TOFPET assembly of example 3 (as well as subject matter of one or more of any combination of examples 2-3, in whole or in part), wherein the angle between the face of the ring and the chest wall-coronal plane is in the range of about 30 degrees to about 60 degrees.

Example 5. The TOFPET assembly of example 3 (as well as subject matter of one or more of any combination of examples 2-, in whole or in part), wherein the angle between the face of the ring and the chest wall-coronal plane is in the range of about 40 degrees to about 50 degrees.

Example 6. The TOFPET assembly of example 3 (as well as subject matter of one or more of any combination of examples 2-5, in whole or in part), wherein the angle between the face of the ring and the chest wall-coronal plane is in the range of about 10 degrees to about 45 degrees.

Example 7. The TOFPET assembly of example 3 (as well as subject matter of one or more of any combination of examples 2-6, in whole or in part), wherein the angle between the face of the ring and the chest wall-coronal plane is in the range of about 45 degrees to about 70 degrees.

Example 8. The TOFPET assembly of example 1 (as well as subject matter of one or more of any combination of examples 2-7, in whole or in part), wherein said timing resolution is in the range of one of the following ranges:

about 100 ps to about 300 ps;
about 150 ps to about 250 ps.
about 200 ps to about 300 ps; or
about 250 ps to about 300 ps.

Example 9. The TOFPET assembly of example 1 (as well as subject matter of one or more of any combination of examples 2-8, in whole or in part), wherein said timing resolution is in the range of: about 300 to about 600 ps;

Example 10. The TOFPET assembly of example 1 (as well as subject matter of one or more of any combination of examples 2-9, in whole or in part), wherein said timing resolution is in the range of one of the following ranges:

about 300 ps to about 400 ps;
about 500 ps to about 600 ps;
about 400 ps to about 500 ps; or
about 400 ps to about 600 ps.

Example 11. The TOFPET assembly of example 1 (as well as subject matter of one or more of any combination of examples 2-10, in whole or in part), further comprising a table for receiving the subject in the prone position, said table including a downward extending aperture for receiving the breast of the subject.

Example 12. The TOFPET assembly of example 1 (as well as subject matter of one or more of any combination of examples 2-11, in whole or in part), wherein said scintillator comprises scintillator crystals.

Example 13. The TOFPET assembly of example 12 (as well as subject matter of one or more of any combination of examples 2-11, in whole or in part), wherein said scintillator crystals comprises at least one of any combination of the following:

Lutetium Orthosilicate (LSO), Lutetium Yttrium Orthosilicate (LYSO), Lutetium Aluminium Perovskite (LuAP), Lutetium Fine Silicate (LFS), Gadolinium Oxyorthosilicate (GSO), Gadolinium-Yttrium Oxyorthosilicate (GYSO), Bismuth Germanate (BGO), Sodium Iodide (NaI(Tl)), Lanthanum Bromide (LaBr3), or Cerium-Doped Lutetium Yttrium Oxyorthosilicate (Ce:LYSO).

Example 14. The TOFPET assembly of example 1 (as well as subject matter of one or more of any combination of examples 2-13, in whole or in part), wherein said detector array occupies about ⅚ of a space defining the ring around the breast.

Example 15. The TOFPET assembly of example 1 (as well as subject matter of one or more of any combination of examples 2-14, in whole or in part), wherein said detector array occupies about ⅔ of a space defining the ring around the breast.

Example 16. The TOFPET assembly of example 1 (as well as subject matter of one or more of any combination of examples 2-15, in whole or in part), wherein said detector array occupies 50% of a space defining the ring around the breast.

Example 17. The TOFPET assembly of example 1 (as well as subject matter of one or more of any combination of examples 2-16, in whole or in part), wherein said ring is circular, elliptical, irregular, or a regular polygon with four equal sides.

Example 18. The TOFPET assembly of example 1 (as well as subject matter of one or more of any combination of examples 2-17, in whole or in part), wherein said detector array comprises separate detector segments that are either:

asymmetrically distributed about a space defining the ring around the breast; or symmetrically distributed about a space defining the ring around the breast.

Example 19. The TOFPET assembly of example 1 (as well as subject matter of one or more of any combination of examples 2-18, in whole or in part), wherein said photomultiplier includes at least one of the following: a standard square photomultiplier, a standard round photomultiplier, a multi-element photomultiplier, a position sensitive flat panel photomultiplier, a position sensitive microchannel plate based photomultiplier, a large size avalanche photodiode with resistive readout, and a silicon photomultiplier array.

Example 20. The TOFPET assembly of example 1 (as well as subject matter of one or more of any combination of examples 2-19, in whole or in part), wherein one of said top edge of one of said detector segments is at least partially under the arm pit of the subject.

Example 21. The method of using any of the devices, assemblies, systems, or their components provided in any one or more of examples 1-20 and 23-42.

Example 22. The method of manufacturing any of the devices, assemblies, systems, or their components provided in any one or more of examples 1-20 and 23-42.

Example 23. A time-of-flight positron emission tomography (TOFPET) assembly for simultaneously detecting lesions of both of a first breast and a second breast of a subject, wherein said subject is anatomically defined with a median plane and chest wall-coronal plane. The assembly comprising: a first detector array and a second detector array having a first detector segment and second detector segment, respectively, wherein said first detector segment and said second detector segment are configured to be located anterior to the subject. The first detector segment and said second detector segment include: a first scintillator and a second scintillator, respectively, for placement toward a target of the respective said first breast and said second breast, said first scintillator and second scintillator each having a top edge generally closest to the subject and a detection surface wall configured to be aligned closest to and at least partially surrounding the respective first breast and the second breast, a first photomultiplier and a second photomultiplier, respectively, located opposite said respective first scintillator and said second scintillator, and a first readout and a second readout, respectively, connected to respective said first photomultiplier and said second photomultiplier. The first detector segment and said second detector segment are configured to acquire tracer emission signals from the target of the respective said first breast and said second breast with a timing resolution of less than about 600 ps. The assembly further comprises: a processor that receives the acquired tracer emission signals and converts the signals into a three dimensional, tomographic image reconstruction thereby representing the simultaneously detection of lesions of both of the first breast and the second breast of the subject. Further, said first detector array and said second detector array are configured having said first detector segment and said second detector segment in a first ring and a second ring, respectively, defining a first face and a second face, respectively, substantially spanning across said first ring and said second ring, respectively. Moreover, said first ring and said second ring are configured to at least partially surround the first breast and the second breast, respectively, and said first face of said first ring and said second face of said second ring being tilted to offset the chest wall-coronal plane of the subject. Further yet, said top edge of one of said first detector segment and said top edge of said second detector segment are above the chest wall-coronal plane of the subject in a posterior direction.

Example 24. The TOFPET assembly of example 23, further comprising:
  a first slant imaging light guide extending from said first scintillator to said first photomultiplier; and
  a second slant imaging light guide extending from said second scintillator to said second photomultiplier.

Example 25. The TOFPET assembly of example 23, wherein:
  an angle between the first face of said first ring and the chest wall-coronal plane is in the range of about 10 degrees to about 80 degrees; and
  an angle between the second face of said second ring and the chest wall-coronal plane is in the range of about 10 degrees to about 80 degrees.

Example 26. The TOFPET assembly of example 23, wherein
  an angle between the first face of said first ring and the chest wall-coronal plane is in the range of about 30 degrees to about 60 degrees; and
  an angle between the second face of said second ring and the chest wall-coronal plane is in the range of about 30 degrees to about 60 degrees.

Example 27. The TOFPET assembly of example 23, wherein:

an angle between the first face of said first ring and the chest wall-coronal plane is in the range of about 40 degrees to about 50 degrees; and
  an angle between the second face of said second ring and the chest wall-coronal plane is in the range of about 40 degrees to about 50 degrees.

Example 28. The TOFPET assembly of example 23, wherein:
  an angle between the first face of said first ring and the chest wall-coronal plane is in the range of about 10 degrees to about 45 degrees; and
  an angle between the second face of said second ring and the chest wall-coronal plane is in the range of about 10 degrees to about 45 degrees.

Example 29. The TOFPET assembly of example 23, wherein
  an angle between the first face of said first ring and the chest wall-coronal plane is in the range of about 45 degrees to about 70 degrees; and
  an angle between the second face of said second ring and the chest wall-coronal plane is in the range of about 45 degrees to about 70 degrees.

Example 30. The TOFPET assembly of example 23, wherein said timing resolution is in the range of one of the following ranges:
  about 100 ps to about 300 ps;
  about 150 ps to about 250 ps.
  about 200 ps to about 300 ps; or
  about 250 ps to about 300 ps.

Example 31. The TOFPET assembly of example 23, wherein said timing resolution is in the range of: about 300 to about 600 ps;

Example 32. The TOFPET assembly of example 23, wherein said timing resolution is in the range of one of the following ranges:
  about 300 ps to about 400 ps;
  about 500 ps to about 600 ps;
  about 400 ps to about 500 ps; or
  about 400 ps to about 600 ps.

Example 33. The TOFPET assembly of example 23, further comprising a table for receiving the subject in a prone position, said table including a downward extending aperture for receiving each of the first breast and the second breast of the subject.

Example 34. The TOFPET assembly of example 23, wherein said first scintillator and said second scintillator comprise scintillator crystals.

Example 35. The TOFPET assembly of example 34, wherein said scintillator crystals comprises at least one of any combination of the following:
  Lutetium Orthosilicate (LSO), Lutetium Yttrium Orthosilicate (LYSO), Lutetium Aluminium Perovskite (LuAP), Lutetium Fine Silicate (LFS), Gadolinium Oxyorthosilicate (GSO), Gadolinium-Yttrium Oxyorthosilicate (GYSO), Bismuth Germanate (BGO), Sodium Iodide (NaI(Tl)), Lanthanum Bromide (LaBr3), or Cerium-Doped Lutetium Yttrium Oxyorthosilicate (Ce:LYSO).

Example 36. The TOFPET assembly of example 23, wherein said first detector array occupies about $\frac{5}{6}$ of a first space defining said first ring around the first breast and said second detector array occupies about $\frac{5}{6}$ of a second space defining said second ring around the second breast.

Example 37. The TOFPET assembly of example 23, wherein said first detector array occupies about $\frac{2}{3}$ of a first space defining said first ring around the first breast and said second detector array occupies about ⅔ of a second space defining said second ring around the second breast.

Example 38. The TOFPET assembly of example 23, wherein said first detector array occupies 50% of a first space defining said first ring around the first breast and said second detector array occupies 50% of a second space defining said second ring around the second breast.

Example 39. The TOFPET assembly of example 23, wherein said first ring and said second ring each are circular, elliptical, irregular, or a regular polygon with four equal sides.

Example 40. The TOFPET assembly of example 23, wherein said first detector array and said second detector array each comprising said first separate detector segment and second separate detector segment, respectively, that are configured to be either:

asymmetrically distributed about a first space defining said first ring around the first breast and a second space defining said second ring around the second breast, respectively; or symmetrically distributed about a first space defining said first ring around the first breast and a second space defining said second ring around the second breast, respectively.

Example 41. The TOFPET assembly of example 23, wherein each of said first photomultiplier and said second photomultiplier includes at least one of the following: a standard square photomultiplier, a standard round photomultiplier, a multi-element photomultiplier, a position sensitive flat panel photomultiplier, a position sensitive microchannel plate based photomultiplier, a large size avalanche photodiode with resistive readout, and a silicon photomultiplier array.

Example 42. The TOFPET assembly of example 23, wherein each of said first detector segment and said second detector segment have a first top edge and a second top edge, respectively, wherein said first top edge of said first detector segment and said second top edge of said second detector segment are configured to be at least partially under the first arm pit and the second armpit, respectively, of the subject.

REFERENCES

The devices, systems, apparatuses, materials, components, computer readable medium, algorithms, and methods of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):

1. U.S. Pat. No. 7,732,774 B2, Majewski, S., "High Resolution Pet Breast Imager with Improved Detection Efficiency", Jun. 8, 2010.
2. U.S. Pat. No. 6,271,525 B1, Majewski, et al., "Mini Gamma Camera, Camera System and Method of Use", Aug. 7, 2001.
3. U.S. Pat. No. 8,698,087 B2, Surti, et al., "Limited Angle Tomography with Time-Of-Flight-PET, Apr. 15, 2014.
4. U.S. Pat. No. 6,946,658 B2, Tai, Y., "Method and Apparatus for Increasing Spatial Resolution of a Pet Scanner", Sep. 20, 2005.
5. International Patent Application No. PCT/US2016/063534, Stuart S. Berr, et al., entitled: "Positron Emission Tomography Systems and Methods", filed Nov. 23, 2016.

6. U.S. Patent Application Publication No. US 2008/0103391 A1, Dos Santos Varela, J., "Tomography by Emission of Positrons (PET) System", May 1, 2008.
7. U.S. Patent Application Publication No. US 2003/0128801 A1, Eisenberg, et al., "Multi-Modality Apparatus for Dynamic Anatomical, Physiological and Molecular Imaging", Jul. 10, 2003.
8. U.S. Pat. No. 6,490,476 B1, Townsend, et al., "Combined PET and X-Ray CT Tomograph and Method for Using Same", Dec. 3, 2002.
9. U.S. Pat. No. 5,825,031, Wong, et al., "Tomographic PET Camera with Adjustable Diameter Detector Ring", Oct. 20, 1998.
10. U.S. Patent Application Publication No. US 2008/0077005 A1, Piron, et al., "System and Method for Multimodality Breast Imaging", Mar. 27, 2008.
11. U.S. Patent Application Publication No. US 2004/0260176 A1, Wollenweber, et al., "Systems and Methods for Correcting a Positron Emission Tomography Emission Image", Dec. 23, 2004.
12. U.S. Patent Application Publication No. US 2011/0192982 A1, Henseler et al., "System and Method for Providing Depth of Interaction Detection Using Positron Emission Tomography", Aug. 11, 2011.
13. U.S. Pat. No. 6,921,901, Chai, et al., "Lutetium Yitrium Orthosilicate Single Crystal Scintillator Detector", Jul. 26, 2005.
14. U.S. Patent Application Publication No. US 2008/0103391 A1, Dos Santos Varela, J., "Tomography by Emission of Positrons (PET System), May 1, 2008.
15. U.S. Patent Application Publication No. US 2003/0128801 A1, Eisenberg, H., et al., "Multi-Modality Apparatus for Dynamic Anatomical, Physiological and Molecular Imaging", Jul. 10, 2003.
16. U.S. Pat. No. 6,490,476 B1, Townsend, D., et al., "Combined PET and X-Ray CT Tomography and Method for Using Same", Dec. 3, 2002.
17. U.S. Pat. No. 5,825,031, Wong, W., et al., "Tomographic PET Camera With Adjustable Diameter Detector Ring", Oct. 20 1988.
18. U.S. Patent Application Publication No. US 2008/0077005 A1, Piron, C., et al., "System and Method for Multimodality Breast Imaging", Mar. 27, 2008.
19. U.S. Patent Application Publication No. US 2004/0260176 A1, Wollenweber, S., et al., "Systems and Methods for Correcting a Positron Emission Tomography Emission Image", Dec. 23, 2004.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A time-of-flight positron emission tomography (TOF-PET) assembly for simultaneously detecting lesions of both of a first breast and a second breast of a subject, wherein said subject is anatomically defined with a median plane and chest wall-coronal plane, said assembly comprising:
    a first detector array and a second detector array that each occupy at least a portion of respective spaces defining rings configured for surrounding the first breast and the second breast, wherein said first detector array and said second detector array each have a first detector segment and a second detector segment,
    wherein for said first detector array and said second detector array, said first detector segment and said second detector segment are each positioned in the assembly and configured for being located anterior to the subject,
    wherein the first detector segment and the second detector segment of each detector array are distributed asymmetrically when configured for positioning relative to the first breast and the second breast;
    wherein said first detector segment and said second detector segment each include:
        a first scintillator and a second scintillator, configured for placement toward a target of said first breast and said second breast;
        a first photomultiplier and a second photomultiplier, located opposite said first scintillator and said second scintillator, and
        a first readout and a second readout, connected to said first photomultiplier and said second photomultiplier;
    wherein said first detector segment and said second detector segment are configured to acquire tracer emission signals from the target of said first breast and said second breast;
    a processor that receives the acquired tracer emission signals and converts the acquired tracer emission signals into a three dimensional, tomographic image reconstruction thereby representing the simultaneous detection of lesions of both of the first breast and the second breast of the subject; and
    wherein for the first detector segment or the second detector segment positioned asymmetrically when relative to the respective breasts and anterior to the subject, a top edge of either said first detector segment or said second detector segment is above the chest wall-coronal plane of the subject and anterior to the subject, wherein the position images a base of the breast at the chest wall-coronal plane,
    wherein for said first detector array and said second detector array:
    said first detector segment and said second detector segment collectively define a first imaging ring and a second imaging ring,
    wherein said first imaging ring comprises a first face and said second imaging ring comprises a second face, said first face and second face configured for being anterior to the subject and configured to at least partially surround the first breast and the second breast, respectively, and said first face or said second face positioned at a tilt configured to define an offset from the chest wall-coronal plane of the subject, wherein the tilt comprises an imaging angle configured for extending from a top edge of the first detector segment or the second detector segment toward the chest wall coronal plane, and wherein the imaging angle is in the range of about 10 degrees to about 80 degrees.

2. The TOFPET assembly of claim 1, further comprising:
a first slant imaging light guide extending from said first scintillator to said first photomultiplier; and
a second slant imaging light guide extending from said second scintillator to said second photomultiplier.

3. The TOFPET assembly of claim 1, wherein
the imaging angle is in the range of about 30 degrees to about 60 degrees.

4. The TOFPET assembly of claim 1, wherein:
the imaging angle is in the range of about 40 degrees to about 50 degrees.

5. The TOFPET assembly of claim 1, wherein:
the imaging angle is in the range of about 10 degrees to about 45 degrees.

6. The TOFPET assembly of claim 1, wherein
the imaging angle is in the range of about 45 degrees to about 70 degrees.

7. The TOFPET assembly of claim 1, wherein said first detector segment and said second detector segment are configured to acquire the acquired tracer emission signals at a timing resolution, and wherein said timing resolution is in the range of one of the following ranges:

about 100 ps to about 300 ps;
about 150 ps to about 250 ps;
about 200 ps to about 300 ps; or
about 250 ps to about 300 ps.

8. The TOFPET assembly of claim 1, wherein said first detector segment and said second detector segment are configured to acquire the acquired tracer emission signals at a timing resolution, and wherein said timing resolution is in the range of about 300 to about 600 picoseconds (ps).

9. The TOFPET assembly of claim 8, wherein said first detector segment and said second detector segment are configured to acquire the acquired tracer emission signals at a timing resolution, and wherein said timing resolution is in the range of one of the following ranges:

about 300 ps to about 400 ps;
about 500 ps to about 600 ps;
about 400 ps to about 500 ps; or
about 400 ps to about 600 ps.

10. The TOFPET assembly of claim 1, further comprising a table configured for receiving the subject in a prone position, said table including a downward extending aperture configured for receiving each of the first breast and the second breast of the subject.

11. The TOFPET assembly of claim 1, wherein said first scintillator and said second scintillator comprise scintillator crystals.

12. The TOFPET assembly of claim 11, wherein said scintillator crystals comprises at least one of any combination of the following:

Lutetium Orthosilicate (LSO), Lutetium Yttrium Ortho-silicate (LYSO), Lutetium Aluminium Perovskite (LuAP), Lutetium Fine Silicate (LFS), Gadolinium Oxyorthosilicate (GSO), Gadolinium-Yttrium Oxy-orthosilicate (GYSO), Bismuth Germanate (BGO), Sodium Iodide (NaI(Tl)), Lanthanum Bromide (LaBr3), or Cerium-Doped Lutetium Yttrium Oxy-orthosilicate (Ce:LYSO).

13. The TOFPET assembly of claim 1, wherein said first detector array occupies about ⅚ of a first space defining a first ring configured for placement around the first breast and said second detector array occupies about ⅚ of a second space a second ring configured for placement around the second breast.

14. The TOFPET assembly of claim 1, wherein said first detector array occupies about ⅔ of a first space defining a first ring configured for placement around the first breast and said second detector array occupies about ⅔ of a second space a second ring configured for placement around the second breast.

15. The TOFPET assembly of claim 1, wherein said first detector array occupies 50% of a first space defining a first ring configured for placement around the first breast and said second detector array occupies 50% of a second space a second ring configured for placement around the second breast.

16. The TOFPET assembly of claim 1, wherein said rings of respective spaces are circular, elliptical, irregular, or a regular polygon with four equal sides.

17. The TOFPET assembly of claim 1, wherein each of said first photomultiplier and said second photomultiplier includes at least one of the following: a standard square photomultiplier, a standard round photomultiplier, a multi-element photomultiplier, a position sensitive flat panel photomultiplier, a position sensitive microchannel plate based photomultiplier, a large size avalanche photodiode with resistive readout, or a silicon photomultiplier array.

18. The TOFPET assembly of claim 1, wherein each of said first detector segment and said second detector segment have a first top edge and a second top edge, respectively, wherein said first top edge of said first detector segment and said second top edge of said second detector segment are configured to be at least partially under the first arm pit and the second armpit, respectively, of the subject.

19. The TOPFET assembly of claim 1, wherein the detector segments comprise detection surface walls that are in different planes relative to each other.

20. A time-of-flight positron emission tomography (TOF-PET) assembly for detecting lesions of a breast of a subject, wherein said subject is anatomically defined with a median plane and chest wall-coronal plane, said assembly comprising:

a detector array having a first detector segment and a second detector segment positioned in the assembly and configured to at least partially surround the breast with both said first and second detector segments anterior to the subject;

wherein said first detector segment comprises a first detection surface wall, and said second detector segment comprises a second detection surface wall, and wherein said first detection surface wall and said second detection surface wall are configured to acquire tracer emission signals from the target of the breast;

a processor that receives the acquired tracer emission signals and converts the acquired tracer emission signals into a three dimensional, tomographic image reconstruction representing the breast of the subject;

said first detection surface wall or second detection surface wall being positioned in the assembly at a tilt configured to offset the first detection surface wall or the second detection surface wall from the chest wall-coronal plane of the subject; and wherein the tilt places a top edge of the first detector segment or a respective top edge of said second detector segment at a position in the assembly configured for placement above the chest wall-coronal plane of the subject and anterior to the subject, wherein the position is configured to image a base of the breast at the chest wall-coronal plane, wherein the tilt comprises an imaging angle configured for extending from the top edge of the first detector segment or the respective top edge of the second detector segment toward the chest wall coronal plane, and wherein the imaging angle is in the range of about 10 degrees to about 80 degrees.

21. The time-of-flight positron emission tomography (TOFPET) assembly of claim 20, wherein said first detector segment and said second detector segment include:

a first scintillator and a second scintillator, respectively, for placement facing the breast of the subject, a first photomultiplier and a second photomultiplier, respectively, located opposite said respective first scintillator and said second scintillator, and a first readout and a second readout, respectively, connected to a respective one of said first photomultiplier and said second photomultiplier and transmitting the tracer emission signals to the processor.

22. The time of flight positron emission tomography (TOFPET) assembly of claim 21, wherein said first detection surface wall or second detection surface wall is configured for placement anterior to a midcoronal plane of the subject.

23. The time of flight positron emission tomography (TOFPET) assembly of claim 21, configured for positioning with the subject in a prone position.

* * * * *